United States Patent
Dagher et al.

(10) Patent No.: US 9,497,964 B2
(45) Date of Patent: Nov. 22, 2016

(54) SYNERGISTIC ACTIVITY OF PERACETIC ACID AND AT LEAST ONE SAR INDUCER FOR THE CONTROL OF PATHOGENS IN AND ONTO GROWING PLANTS

(75) Inventors: Fadi Dagher, Laval (CA); Marco Cassandra, Laval (CA)

(73) Assignee: AGRI-NEO INC., Ontario (CA)

( * ) Notice: Subject to any disclaimer, the term of this patent is extended or adjusted under 35 U.S.C. 154(b) by 435 days.

(21) Appl. No.: 13/880,887

(22) PCT Filed: Sep. 28, 2011

(86) PCT No.: PCT/CA2011/001091
§ 371 (c)(1),
(2), (4) Date: Apr. 22, 2013

(87) PCT Pub. No.: WO2012/051699
PCT Pub. Date: Apr. 26, 2012

(65) Prior Publication Data
US 2013/0259957 A1   Oct. 3, 2013

Related U.S. Application Data

(60) Provisional application No. 61/405,849, filed on Oct. 22, 2010.

(51) Int. Cl.
*A01N 37/16* (2006.01)
*A01N 59/00* (2006.01)

(52) U.S. Cl.
CPC ............... *A01N 37/16* (2013.01); *A01N 59/00* (2013.01)

(58) Field of Classification Search
CPC ...... A01N 25/12; A01N 37/16; A01N 59/00; A01N 2300/00
See application file for complete search history.

(56) References Cited

U.S. PATENT DOCUMENTS

| | | | |
|---|---|---|---|
| 2,512,640 A | 6/1950 | Greenspan et al. | |
| 5,168,655 A | 12/1992 | Davidson et al. | |
| 5,607,856 A | 3/1997 | Moon et al. | |
| 5,614,203 A | 3/1997 | Dezur et al. | |
| 5,718,910 A | 2/1998 | Oakes et al. | |
| 5,723,406 A | 3/1998 | Larose et al. | |
| 5,733,474 A | 3/1998 | Kagermeier et al. | |
| 5,965,033 A | 10/1999 | Huss et al. | |
| 6,024,986 A | 2/2000 | Hei | |
| 6,096,226 A | 8/2000 | Fuchs et al. | |
| 6,165,483 A | 12/2000 | Hei et al. | |
| 6,238,685 B1 | 5/2001 | Hei et al. | |
| 6,455,075 B1 | 9/2002 | Larose | |
| 6,514,556 B2 | 2/2003 | Hilgren et al. | |
| 6,582,961 B1 | 6/2003 | Moon et al. | |
| 6,627,593 B2 | 9/2003 | Hei et al. | |
| 6,627,657 B1 | 9/2003 | Hilgren et al. | |
| 6,635,286 B2 | 10/2003 | Hei et al. | |
| 6,682,697 B2 | 1/2004 | He et al. | |
| 6,797,302 B1 | 9/2004 | Ben Yehuda et al. | |
| 6,827,766 B2 | 12/2004 | Carnes et al. | |
| 6,946,155 B2 | 9/2005 | Ben Yehuda et al. | |
| 6,962,714 B2 | 11/2005 | Hei et al. | |
| 7,005,549 B2 | 2/2006 | Hobson et al. | |
| 7,052,911 B2 | 5/2006 | Moon et al. | |
| 7,147,872 B2 | 12/2006 | Ben-Yehuda et al. | |
| 7,291,276 B1 | 11/2007 | Zahn | |
| 7,307,191 B2 | 12/2007 | Hobson et al. | |
| 7,326,824 B2 | 2/2008 | Campbell et al. | |
| 7,368,121 B2 | 5/2008 | Larose | |
| 7,615,187 B2 | 11/2009 | Helton et al. | |
| 7,622,606 B2 | 11/2009 | Smith et al. | |
| 7,691,630 B2 | 4/2010 | Moon et al. | |
| 7,816,555 B2 | 10/2010 | Smith et al. | |
| 7,832,360 B2 | 11/2010 | Hilgren et al. | |
| 8,062,676 B2 | 11/2011 | Besendorfer | |
| 8,246,758 B2 | 8/2012 | Man et al. | |
| 2003/0114310 A1 | 6/2003 | Silverman | |
| 2003/0206964 A1 | 11/2003 | Larose | |
| 2003/0207014 A1 | 11/2003 | Larose et al. | |
| 2003/0228733 A1 | 12/2003 | Itoh et al. | |
| 2004/0014601 A1 | 1/2004 | Moon et al. | |
| 2004/0162228 A1 | 8/2004 | Hobson et al. | |

(Continued)

FOREIGN PATENT DOCUMENTS

| | | |
|---|---|---|
| CA | 2353645 | 6/2000 |
| CA | 2353645 A1 | 6/2000 |

(Continued)

OTHER PUBLICATIONS

Ma, "Role of Silicon in Enhancing the Resistance of Plants to Biotic and Abiotic Stresses", 2004, Soil Science and Plant Nutrition, vol. 50, issue 1, pp. 11-18.*
Inhibitory Mechanisms of Two Silicon Compounds on Mildew Powder of Melon, Guo et al, dated Mar. 31, 2005.
Guo et al., "Inhibitory Mechanisms of Two Silicon Compounds on Mildew Powder of Melon", 2005, 38(3):576-581.
PCT International Search Report for PCT/CA2011/001091, dated Jan. 9, 2012.
F.P. Greenspan and D.G. MacKellar, 1948, Anal. Chemistry, vol. 20, No. 11, Nov. 1948, pp. 1061-1062.

(Continued)

*Primary Examiner* — Michael B Pallay
(74) *Attorney, Agent, or Firm* — Dority & Manning, P.A.

(57) ABSTRACT

A method for controlling pathogens on a plant tissue of a growing plant with an aqueous solution resulting from the dissolution in water of a powdered composition comprising a dry, water soluble mixture of (i) a peracetic acid precursor comprising: a solid hydrogen peroxide precursor, optionally a pH adjusting agent, and an acetylating agent; and (ii) at least one SAR inducer which is a water soluble silicate salt defining a source of silicate ions, to generate in situ peracetic acid (PAA). A synergistic effect is observed once the SAR inducer which is a water soluble silicate salt defining a source of silicate ions, and the peracetic acid are respectively simultaneously present in and on the plant.

24 Claims, No Drawings

(56) References Cited

U.S. PATENT DOCUMENTS

| | | | |
|---|---|---|---|
| 2005/0234021 A1* | 10/2005 | Petasis | A01N 57/18 514/79 |
| 2006/0029631 A1 | 2/2006 | Larose | |
| 2006/0205598 A1* | 9/2006 | Moon | A01N 37/16 504/116.1 |
| 2006/0258535 A1 | 11/2006 | Larose | |
| 2007/0197388 A1 | 8/2007 | Vunk et al. | |
| 2008/0139435 A1 | 6/2008 | MacGregor | |
| 2008/0194689 A1 | 8/2008 | Reichwagen | |
| 2008/0214425 A1* | 9/2008 | Lant et al. | 510/300 |
| 2008/0262098 A1 | 10/2008 | Willuweit | |
| 2009/0004167 A1 | 1/2009 | Boulos et al. | |
| 2009/0305888 A1 | 12/2009 | Li et al. | |
| 2009/0312292 A1 | 12/2009 | Rovison et al. | |
| 2010/0092574 A1 | 4/2010 | Sweeny | |
| 2010/0160449 A1 | 6/2010 | Rovison et al. | |
| 2010/0179368 A1* | 7/2010 | Conrad | A01N 37/16 588/299 |
| 2011/0220155 A1 | 9/2011 | Man et al. | |

FOREIGN PATENT DOCUMENTS

| | | |
|---|---|---|
| CA | 2569025 | 6/2008 |
| CA | 2569025 | 1/2013 |
| CA | 2353645 | 3/2013 |
| CN | 1543794 | 11/2004 |
| EP | 648 418 | 4/1995 |
| EP | 720 814 | 7/1996 |
| EP | 0 967 175 | 12/1999 |
| EP | 0 968 188 | 1/2000 |
| EP | WO2009027857 A1 | 3/2009 |
| FR | 2 728 171 | 6/1996 |
| GB | 2 169 308 | 7/1986 |
| GB | 2 268 879 | 1/1994 |
| GB | 2 355 198 | 4/2001 |
| JP | H11061183 | 5/1999 |
| JP | 4436659 | 3/2010 |
| WO | WO 92/19287 | 11/1992 |
| WO | WO 95/02330 | 1/1995 |
| WO | WO0183664 A1 | 11/2001 |
| WO | WO 2007/092180 | 8/2007 |
| WO | WO 2010/006233 | 1/2010 |

OTHER PUBLICATIONS

Inhibitory Mechanisms of Two Silicon Compounds on Mildew Powder of Melon, Guo et al, dated Mar. 31, 2005.

* cited by examiner

SYNERGISTIC ACTIVITY OF PERACETIC ACID AND AT LEAST ONE SAR INDUCER FOR THE CONTROL OF PATHOGENS IN AND ONTO GROWING PLANTS

FIELD OF THE INVENTION

The invention relates to the field of agriculture. It concerns an unexpected synergistic activity resulting from a combined use of peracetic acid and at least one SAR inducer for the control of pathogens into and on a plant tissue of a growing plant. Also, the invention relates to a water soluble mixture or composition (especially a powdered composition) comprising a peracetic precursor system and at least one SAR inducer, which once admixed with water, allow the control of pathogens in and onto a plant tissue of a growing plant. Also, the invention relates to uses and methods involving said water soluble mixture or composition, and a kit comprising said water soluble mixture or composition.

BACKGROUND OF THE INVENTION

Peracetic acid ($C_2H_4O_3$) in an aqueous solution is a mixture which is further comprising acetic acid ($CH_3COOH$) and hydrogen peroxide ($H_2O_2$). Typically, peracetic acid (PAA) is produced by reacting acetic acid and hydrogen peroxide. It is also well known to generate a liquid solution comprising PAA starting from the dissolution of a powdered mixture (U.S. Pat. No. 7,291,276; UK patent application No. 2,355,198; FR patent application 2,728,171; Canadian patent application No. 2,569,025; International PCT patent application WO 95/02330 and EP patent application No. 0 648 418).

Peracetic acid (also known as peracid) is a strong oxidizing agent which is known for having virucidal, bactericidal, fungicidal and algicidal properties. Peracetic acid was patented in 1950 for the treatment of raw plant tissue, especially for the treatment of fruits and vegetables, to reduce spoilage from bacteria and fungi destined for processing (U.S. Pat. No. 2,512,640). Nowadays, peracetic acid his commonly use in food processing and handling as a sanitizer for food contact surfaces and as a disinfectant for fruits, vegetables, meat and eggs (NOSB TAP Materials database compiled by OMRI, Nov. 3, 2000, 7 pages). In the production of fruits and vegetables, peracetic aqueous solutions have been suggested to control pathogenic organisms on growing plants (U.S. Pat. No. 6,024,986; U.S. Pat. No. 6,165,483; and U.S. Pat. No. 6,238,685).

One of the problems associated with liquid peracetic aqueous solutions is that these solutions are corrosive, highly acidic, and dangerously reactive. There is thus a need for a mixture or a composition, preferably a powdered mixture, containing or capable of generating peracetic acid in situ in concentration and at a pH which is safe for plants.

In performing extensive searches to find a solution to the above-mentioned needs, which needs includes more efficient mixture, composition, use and kits for the control of pathogenic organisms in and onto growing plants, the Applicant has surprisingly discovered an unexpected synergistic activity between peracetic acid and at least one SAR inducer, for the control of pathogens into and on a plant tissue of a growing plant.

Furthermore, there is a need for mixtures, compositions, methods, uses and kits based on the above-mentioned synergistic activity, where the rate of generation of the peracetic acid can be controlled, especially when said rate of generation needs to be faster or lower in view of an optimized the synergistic activity of said peracetic acid with said at least one SAR inducer.

The present invention further addresses aforesaid needs and other needs as it will be apparent from review of the disclosure, drawings and description of the features of the invention hereinafter.

BRIEF SUMMARY OF THE INVENTION

An embodiment of the invention relates to a composition comprising a water soluble mixture of
(i) a peracetic acid precursor comprising:
a) hydrogen peroxide, hydrogen peroxide precursor or a mixture thereof,
b) optionally a pH adjusting agent, and
c) an acetylating agent; and
(ii) at least one SAR inducer which is a water soluble silicate salt defining a source of silicate ions;
wherein said composition generates peracetic acid (PAA) upon addition of water.

Another embodiment of the invention relates to a powdered composition comprising a dry, water soluble mixture of
(i) a peracetic acid precursor comprising:
a) a solid hydrogen peroxide precursor,
b) optionally a pH adjusting agent, and
c) an acetylating agent; and
(ii) at least one SAR inducer which is a water soluble silicate salt defining a source of silicate ions;
wherein said composition generates in situ peracetic acid (PAA) upon addition of water.

As used herein, the term "acetylating agent" refers to any suitable product which is capable of reacting in solution with the solid hydrogen peroxide precursor for generating peracetic acid. Examples include acetylsalicylic acid and tetraacetylethylenediamine (TAED).

According to a particularly preferred embodiment, the acetylating agent is TAED. Upon addition of water (e.g. dissolution of the mixture) it will be possible to obtain an aqueous solution where the solid hydrogen peroxide and the TAED will react and generate peracetic acid (PAA). The principles of reaction: this reaction is summarized by the following equation:

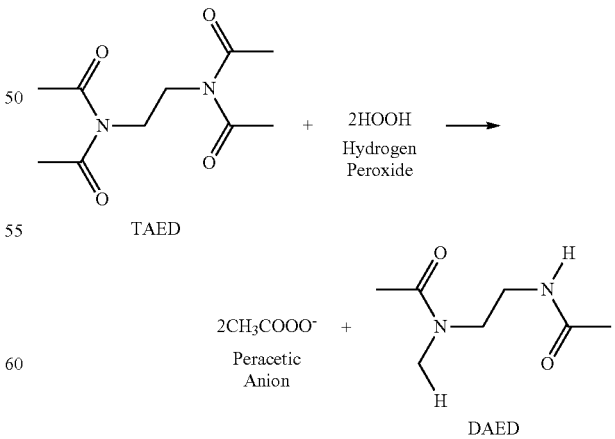

According to a particularly preferred embodiment, the term "solid hydrogen peroxide precursor" refers to any suitable dry product which is capable of generating hydrogen peroxide once dissolved in water. Suitable examples according to the invention include, but are not limited to, sodium percarbonate (coated or not), sodium peroxyhydrate, sodium perborate monohydrate, sodium perborate tetrahydrate, sodium persulfate, potassium perborate, ammonium percarbonate. In preferred embodiments, the solid hydrogen peroxide is coated sodium percarbonate. Once coated, the sodium percarbonate is provided with at least one coat of a substance allowing improvement of storage and rheology. The nature of the coating does not significantly affect the efficiency of aqueous composition to be obtained.

According to a particularly preferred embodiment, the term "pH adjusting agent" refers to any suitable dry product which is capable of adjusting pH of the aqueous solution. Examples of suitable pH adjusting agents according to the invention include, but are not limited to, citric acid, phosphoric acid, nitric acid, hydrochloric acid, glycolic acid, weak acids (e.g. formic acid, acetic acid, hydrofluoric acid, nitrous acid, hydrocyanic acid, benzoic acid), organic acids (e.g. carboxylic acid, lactic acid, acetic acid, citric acid, oxalic acid) and sulfamic acid. In preferred embodiments, the pH adjusting agent is citric acid. It is within the knowledge of those skilled in the art to identify and select a pH adjusting agent which can reduce the pH according to the invention.

According to a particularly preferred embodiment, the SAR inducer may be selected amongst a broad list of SAR inducers known to the skilled workman, and more preferably it may be a pesticide or a biopesticide which refer to any suitable product which can provide a source of silicate ions, more preferably a water soluble silicate salt, more preferably a potassium silicate. Preferably, such a biopesticides may also represent but are not limited to, potassium silicate, sodium silicate, sodium metasilicate. In preferred embodiments, the biopesticide is potassium silicate and it can provide both, potassium and silicate.

According to a particularly preferred embodiment, the sequestering agent is an optional ingredient of the powered composition. As used herein, the term "sequestering agent" may refer to any suitable chelants, chelators, or chelating agents which may be helpful in stabilizing hydrogen peroxide and peracetic acid in the aqueous solution. Suitable sequestering agents may include those compounds which chelate metal ions (e.g. calcium, magnesium, manganese, iron, copper, aluminum, etc.) that may attack hydrogen peroxide and peracetic acid. Examples of suitable sequestering agents according to the invention include, but are not limited to, ethylenediaminetetraacetic acid (EDTA), nitrilotriacetic acid (NTA), and phosphonates. In particularly preferred embodiments, the sequestering agent may be EDTA. The sequestering agent may be preferably used in a dry form, but given it is present in relatively low amount, it is also conceivable that it could be added to the powdered composition under a liquid form (e.g. sprayed).

Since preferred embodiments concerns agricultural uses (e.g. human consumption) those skilled in the art will understand that preferred compounds include those compounds which are non-toxic to human, and more preferably those certified as "food grade". Furthermore, the solid hydrogen peroxide, the optional pH adjusting agent, the acetylating agent (e.g. tetraacetylethylenediamine (TAED)), the SAR inducer, and the optional sequestering agent are preferably selected in proportions maximizing generation of peracetic acid, while remaining non-toxic to plants and more preferably, they are at concentrations providing beneficial effects on controlling pathogenic organisms and eventually, concerning some possible SAR inducers, further contributing as a collateral effect, to the fertilization of the soils (e.g. addition of potassium ions to the soil). The compounds comprised in the composition according to the invention are commercially available and may be purchased from many suppliers such as Univar Canada Ltd, Brenntag, Kingsfield inc., Debro Chemicals, Warwick International Limited, and/or MultiChem®.

In preferred embodiments, the powdered composition of the invention may be marketed as concentrate and an end user dilutes the concentrate to a use aqueous solution. The level of active components in the powdered composition may be dependent upon the intended dilution factor and desired activity in the use solution. In one particular embodiment, the mixture is formulated such that 2 g of the powdered composition in 1000 g of water generates about 200 ppm of peracetic acid (PAA) at pH 7.0±3.0. This may occur within about 1 min to 24 hrs.

Those skilled in the art know how to monitor levels of peracetic in solutions. For instance, it is known to use iodometric titration (F. P. Greenspan and D. G. MacKellar, 1948, *Anal. Chem.*, 20, 1061) or to use analytical test strips. Suitable test strips include those manufactured by Merck and which are currently available under two different formats (i.e. 5-50 ppm and 100-500 ppm). These test strips provide a rapid, convenient semi-quantitative method of determining peracetic levels. LaMotte Company (Chestertown, Md., USA) also provides a test kit (code 7191-01) for titrating peracetic acid.

In addition, the powered compositions of the invention may also contain additional ingredients, including but not limited to, metal chelators, metal scavengers, coating agents, preserving agents, solubilizing agents, stabilizing agents, wetting agents, emulsifiers, colorants (e.g. tracer dyes), odorants, salts, buffers, surfactants, solvents, coating agents and/or antioxidants. For preparing the composition of the invention, methods well known in the art may be used.

The powdered compositions of the invention may be packaged under different forms, such as a pouch (e.g. bag), a tablet (e.g. puck), or a sealed container (e.g. bucket, plastic bottle, a plastic pail, a plastic drums, a plastic totes), etc.

Agricultural uses: Those skilled in the art will readily appreciate that the mixture or compositions of the invention possesses numerous beneficial properties. For instance, aqueous solutions prepared using such mixture or composition may increase plant growth by providing oxygen to plant roots and act as a bactericide and fungicide by releasing hydrogen peroxide and peracetic acid. The SAR inducer (Systemic Acquired Resistance) stimulates the plant natural defenses to diseases (e.g. powdery mildew, gray mold rot (*Botrytis cinerea*) on blueberry) and pests (e.g. mites, aphids, whiteflies). The combined use of peracetic acid and at least one SAR inducer, more preferably a SAR inducer defining a biopesticide comprising silicate ions, surprisingly shows a synergistic activity, especially but not limitatively, an amplification of plant defense responses to fungal infection, thereby enhancing the plant defenses against attack from powdery mildew, and other fungal diseases and insects, improving resistance to mineral stress, decreasing climate stress and further improving overall strength and increasing growth and yield.

Accordingly, additional aspects of the invention relates to methods for controlling microbial pathogens on a plant tissue of a growing plant. As used herein, the term "microbial pathogen" refers to any microorganism susceptible to harm a living plant, damage a living plant or negatively influence the viability or growth of a living plant. The term microbial pathogen encompasses viruses, bacteria, yeast, mold and oomycetes.

The invention encompasses controlling microbial pathogens including, but not limited to gram positive and gram negative bacteria. Bacteria against which the methods and compositions of the invention may be useful include, but are not limited to, *Agrobacterium, Clavibacter, Erwinia, Pseudomonas, Xanthomonas, Streptomyces*, and *Xylella*.

The invention encompasses controlling microbial pathogens including, but not limited to viruses. Viruses against which the methods and compositions of the invention may be useful include, but are not limited to, Sharka (Plum pox potyvirus) D, M, C, Ea serogroups; Lettuce infectious yellows crinivirus; Tomato infectious yellows crinivirus; Tomato chlorosis crinivirus; Lettuce chlorosis crinivirus; Cucurbit yellow stunting disorder crinivirus; Sweet potato chlorotic stunt crinivirus; High Plains virus (sometimes complexed with wheat streak mosaic virus); Citrus tristeza closterovirus; Citrus tatterleaf capillovirus; Citrus chlorotic dwarf (unknown virus); Tomato spotted wilt tospovirus; Impatiens necrotic spot tospovirus; Tomato yellow leaf curl geminivirus; Raspberry bushy dwarf idaeovirus; Blueberry shock ilarvirus.

The invention encompasses controlling microbial pathogens including, but not limited to yeast, mold (fungi), and oomycetes. Yeast, mold (fungi) and oomycetes against which the methods and compositions of the invention may be useful include, but are not limited to, *Fusarium* spp. (causal agents of *Fusarium* wilt disease); *Thielaviopsis* spp. (causal agents of: canker rot, black root rot, *Thielaviopsis* root rot); *Verticillium* spp.; *Magnaporthe grisea* (T. T. Hebert) M. E. Barr; causes blast of rice and gray leaf spot in turfgrasses; *Rhizoctonia* spp.; *Phakospora pachyrhizi* Sydow (causes Soybean rust); *Puccinia* spp.; the genus *Phytophthora* (includes the causal agents of potato late blight and sudden oak death; *Pythium* spp.; *Phytophthora* spp).

The invention encompasses controlling microbial pathogens which may be harmful to humans. Human pathogens against which the methods and compositions of the invention may be useful include, but are not limited to, *Escherichia coli, Staphylococcus aureus, Salmonella* species, *Listeria* species, *Mycobacterium tuberculosis*, and viruses responsible for humans diseases such as flu, foot and mouth disease, swine fever, etc.

The methods and compositions of the invention may be beneficial to many different plants and tissues. Examples of plant tissue encompassed by the present invention include, but are not limited to, the leaves, stems, flowers, fruits, tubers, corms, roots, etc. In preferred embodiment, the plant tissue is a leaf.

Examples of plants encompassed by the present invention include, but are not limited to, fruit (such as apricot, apple, banana, berry, blackberry, blueberry, cherry, cranberry, currant, greengage, grape, grapefruit, gooseberry, lemon, mandarin, melon, orange, pear, peach, pineapple, plum, raspberry, strawberry, sweet cherry, watermelon, wild strawberry, etc.), vegetables (such as artichoke, bean, beetroot, broad bean, broccoli, cabbage, carrot, cauliflower, celery, chicory, chives, cress, corn, cucumber, curly kale, dill, eggplant, garlic, kohlrabi, lettuce, onion, paprika, parsnip, parsley, pea, pore, pumpkin, radish, shallot, small radish, spinach, swede turnip, tomato, turnip, etc.) and flowers (such as Amaryllis, Aster, Anemone, Azalea, Begonia, Bluebell, Baby's Breath, Chrysanthemum, Clover, Crocus, Freesia, Gladiola, Lily, Daisy, Bee Balm, Bergamot, Bell Flower, Bird of Paradise, Bottlebrush, Calla Lily, Columbine, Orchid, Daffodil, Primrose, Forget-Me-Not, Foxglove, Iris, Lilac, Marjoram, Orange Blossom, Peach Blossom, Petunia, Rosemary, Sage, Thyme, Thistle, Hyacinth, Lady's Slipper, Amaranthus, Marigold, Mimosa, Peony, Rose, Holly, Lavender, Snapdragon, Carnation, Sunflower, Tansy, Tulip, Buttercup, Zinnia, etc.), turf grasses and long grasses.

More particularly, the plant may be selected from the group consisting of baking apples, eating apples, sauce apples, apricot, banana, blackberry, blueberry, cantaloupe, cherry, cranberry, currant, raisin grapes, seed grapes, table grapes, wine grapes, greengage, gooseberry, honeydew, lemon, mandarin, melon, orange, peach, Anjou pears, Asian pears, Bartlett pears, Bosc pears, Cornice pears, Red Bartlett pears, Seckel pears, pineapple, plum, raspberry, strawberry, sweet cherry, watermelon, wild strawberry, artichoke, bean, beetroot, broad bean, broccoli, cabbage, Argentine canola, Polish canola, seed canola, carrot, cauliflower, celery, chicory, chives, cress, burpless cucumbers, pickling cucumbers, slicing cucumbers, space-saver cucumbers, specialty cucumbers, curly kale, dill, eggplant, kohlrabi, butterhead lettuces, cos/romaine lettuces, crisphead lettuces, looseleaf lettuces, seed lettuces, onion, paprika, parsnip, parsley, pea, baking potatoes, boiling potatoes, frying potatoes, seed potatoes, pumpkin, radish, shallot, small radish, field/oil soybean, seed soybean, vegetable/garden soybean, spinach, beefsteak tomatoes, campari tomatoes, cherry tomatoes, paste-drying tomatoes, plum tomatoes, salad tomatoes, slicing/globe tomatoes, swede turnip, and turnip.

More particularly, the plant may be selected from the group consisting of amaranth, canola, culinary barley, malting barley, livestock feed/silage barley, seed barley, buckwheat, livestock feed corn, ornamental corn, popping corn, seed corn, silage corn, sweet corn, starch corn, fonio, kamut, millet, culinary oats, livestock feed/silage oats, seed oats, quinoa, African rice, Australian rice, Caribbean rice, Far Eastern rice, Indian subcontinent rice, Middle Eastern rice, North American rice, seed rice, Southeast Asian rice, Spanish rice, wild rice, rye, sorghum, spelt, teff, triticale, durum wheat, spring wheat, spring spelt wheat, winter wheat, and winter spelt wheat.

Other non limitative examples of plants may include roots such as potatoes, or cereals such as corn, rice, wheat, barley, sorghum, millet, oats, ryes, triticale, fonio, teff, buckwheat, quinoa, etc.

The aqueous solutions prepared with the powdered composition according to the invention may have many beneficial effects on growing plants including, but not limited to, controlling microbial pathogens; protecting the plant against microbial pathogens, promoting natural defense of the plant, providing oxygen to roots of the plant, providing essential nutrients to the plant.

According to a particularly preferred embodiment, the expression "controlling" includes, but is not limited to, preventing a microbial pathogen infection, inhibiting or slowing growth of microbial pathogen(s), killing, and/or eradicating the microbial pathogen(s), etc. The methods and compositions according to the invention may be used in both curative and preventive programs.

According to a particularly preferred embodiment, in some embodiments, the aqueous solution which is used for treating the plant tissue comprises about 20 ppm, or about 50 ppm, or about 75 ppm, or about 100 ppm, or about 200 ppm, or about 300 ppm, or about 400 ppm, or about 500 ppm, or about 750 ppm, or about 1000 ppm, or about 1500 ppm or about 2000 ppm of peracetic acid (PAA). The solution is preferably at pH 7.0±3.0, but depending on the particular uses in could be as low as pH 4±2.0 and as high as pH 9.5±2.0.

According to a particularly preferred embodiment, the present invention contemplates a powdered composition which is dissolved to obtain a diluted aqueous solution prior to its utilization in controlling plants microbial pathogens. For safety and economical reasons, in a preferred embodiment, the powdered composition would be marketed as a concentrate and the end user would dilute the concentrate with water to a use solution. The level of active components in the concentrate powdered composition and/or diluted solution will be dependent upon the intended dilution factor and desired activity in the use solution.

According to a particularly preferred embodiment, the aqueous solutions according to the invention can be applied to the plant tissue in a variety of techniques. For instance, the aqueous solution can be sprayed, painted, daubed, fogged, onto or into the plant, the plant hydroponic substrate, the agricultural earth (e.g. irrigation). The solution can be reapplied periodically as needed.

According to a particularly preferred embodiment, another aspect of the invention pertains to commercial packages or kits for using the compositions and carrying out the methods of the invention. Kits according to the invention may be used for preparing aqueous solutions for use in controlling microbial pathogens on a plant tissue of a growing plant.

According to a particularly preferred embodiment, an additional aspect of the invention related to kits. In one embodiment, the kit includes a container (e.g. a pouch, a tablet, a bucket, etc.) comprising a powdered composition as defined herein, and a user manual or instructions. A kit of the invention may further comprise one or more of the following elements: test strips for determining peracetic levels, test strips for determining hydrogen peroxide levels, test kits for determining peracetic acid levels.

According to a particularly preferred embodiment, the powdered compositions according to the invention would be marketed as a concentrate to be diluted by an end user. It is also conceivable according to the invention to provide the end user with separate containers comprising individually the active components of the powdered composition according to the invention. The end user will then mix himself the active components for achieving an intended dilution factor and a desired activity.

Therefore, a kit or commercial package according to that particular embodiment would comprises a plurality of individual containers (e.g. pouch, tablet, bucket, etc.), and a user manual or instructions, the individual containers each comprising at least one of a solid hydrogen peroxide, a pH adjusting agent, and tetraacetylethylenediamine (TAED). Individual containers (same or additional containers) further comprise at least a biopesticide comprising a water soluble silicate salt, more preferably a potassium silicate and sequestering agent(s).

Another embodiment of the invention relates to the powdered composition defined hereinabove, wherein said at least one SAR inducer which is a water soluble silicate salt defining a source of silicate ions, is selected from the group consisting of:
at least one pesticide comprising a water soluble silicate salt,
at least one biopesticide comprising a water soluble silicate salt, and
silica/silicate.

Another embodiment of the invention relates to the powdered composition defined hereinabove, wherein the dry, water soluble mixture comprises:
(i)-a) about 30-60% w/w of the solid hydrogen peroxide precursor,
(i)-b) about 10-40% w/w the pH adjusting agent,
(i)-c) about 10-40% w/w of the acetylating agent; and
(ii) about 1-30% w/w of the at least one biopesticide comprising the water soluble silicate salt which is defining a source of silicate ions;
wherein (i)-a), (i)-b) and (i)-c) represent the peracetic acid precursor; and wherein when 2 g of said dry, water soluble mixture of (i)-a), (i)-b), (i)-c) and (ii) is admixed with 1000 g of water, about 100 to 250 ppm of peracetic acid (PAA) are generated in situ at pH 7.0±3.

Another embodiment of the invention relates to the powdered composition defined hereinabove, further comprising a sequestering agent.

Another embodiment of the invention relates to the powdered composition defined hereinabove, wherein it further comprises from 0.01 to 10% w/w of a sequestering agent.

Another embodiment of the invention relates to the powdered composition defined hereinabove, wherein it further comprises at least one surfactant.

Another embodiment of the invention relates to the powdered composition defined hereinabove, wherein the surfactant is an anionic surfactant, a nonionic surfactant, a cationic surfactant or an amphoteric surfactant.

Another embodiment of the invention relates to the powdered composition defined hereinabove, wherein the surfactant is
an anionic surfactant selected from the group consisting of carboxylates, sulfonates, petroleum sulfonates, alkylbenzenesulfonates, naphthalene sulphonates, olefin sulphonates, alkyl sulphates, sulphated natural oils, sulphated natural fats, sulphated esters, sulphated alkanolamides, sulphated alkanolamides, alkylphenols ethoxylated and alkylphenols sulphated; or
a non-ionic surfactant selected from the group consisting of ethoxylated aliphatic alcohol, polyoxyethylene surfactants, carboxylic esters, polyethylene glycol esters, anhydrosorbitol ester and its ethoxylated derivarives, glycol esters of fatty acids, carboxylic amides, monoalkanolamine condensates and polyoxyethylene fatty acid amides; or
a cationic surfactant selected from the group consisting of quarternary ammonium salts, amines with amide linkages, polyoxyethylene alkyl and alicyclic amines, 4-N, N,N',N'-tetrakis substituted ethylenediamines and 5,2-alkyl-1-hydroxyethyl 2-imidazolines; or
an amphoteric surfactant selected from the group consisting of N-coco 3-aminopropionic acid and its sodium salt, N-tallow 3-iminodipropionate and its disodium salt, N-carboxymethyl N-dimethyl N-9 octadecenyl ammonium hydroxide, and N-cocoamidethyl N-hydroxyethylglycine and its sodium salt.

Another embodiment of the invention relates to the powdered composition defined hereinabove, wherein the surfactant is an alpha olefin sulfonate.

Another embodiment of the invention relates to the powdered composition defined hereinabove, wherein it further comprises up to 4% by weight of a surfactant consisting of an alpha olefin sulfonate having from 12 to 18 carbon atoms.

Another embodiment of the invention relates to the powdered composition defined hereinabove, wherein the dry, water soluble mixture comprises:

(i)-a) about 43.5% w/w of the solid hydrogen peroxide precursor,
(i)-b) about 25% w/w the pH adjusting agent,
(i)-c) about 21% w/w of the acetylating agent;
(ii) about 10% w/w of the at least one biopesticide comprising the water soluble silicate salt which is defining a source of silicate ions; and
(iii) about 0.5% w/w of the sequestering agent;
wherein (i)-a), (i)-b) and (i)-c) represent the peracetic acid precursor; and wherein when 2 g of said dry, water soluble mixture of (i)-a), (i)-b), (i)-c), (ii) and (iii) is admixed with 1000 g of water, about 100 to 250 ppm of peracetic acid (PAA), preferably 200 ppm of peracetic acid (PAA), are generated in situ at pH 7.0±2, preferably 7.0±1.5 and more preferably 7.0±1.0.

Another embodiment of the invention relates to the powdered composition defined hereinabove, wherein wherein the dry, water soluble mixture comprises:
(i)-a) about 50% w/w of the solid hydrogen peroxide precursor,
(i)-b) about 15% w/w the pH adjusting agent,
(i)-c) about 20% w/w of the acetylating agent;
(ii) about 10% w/w of the at least one biopesticide comprising the water soluble silicate salt which is defining a source of silicate ions;
(iii) about 1% w/w of the sequestering agent;
(iv) about 4% w/w of a surfactant as defined hereinabove; and
wherein (i)-a), (i)-b) and (i)-c) represent the peracetic acid precursor; and wherein when 2 g of said dry, water soluble mixture of (i)-a), (i)-b), (i)-c), (ii), (iii) and (vi) is admixed with 1000 g of water, about 100 to 250 ppm of peracetic acid (PAA) are generated in situ at pH 8.0±3, preferably 8.5±2.0 and more preferably 8.5±1.5.

Another embodiment of the invention relates to the powdered composition defined hereinabove, wherein the sequestering agent is an inorganic acid, an organic acid or a mixture of at least two acid selected from the group consisting of inorganic acids and organic acids.

Another embodiment of the invention relates to the powdered composition defined hereinabove, wherein the sequestering agent is EDTA, NTA, DTPA, or Phosphonates.

Another embodiment of the invention relates to the powdered composition defined hereinabove, wherein the sequestering agent is
ethylenediaminetetraacetic acid (EDTA),
nitrilotriacetic Acid (NTA),
diethylenetriaminepentaacetic acid (DTPA),
1-hydroxyethane(1,1-diylbiphosphonic acid) (HEDP),
nitrilotris(methylenephosphonic acid) (NTMP),
diethylenetriaminepentakis(methylenephosphonic acid) (DTPMP),
1,2-diaminoethanetetrakis(methylenephosphonic acid) (EDTMP),
sodium salt of 1,2-diaminoethanetetrakis(methylenephosphonic acid),
potassium salt of 1,2-diaminoethanetetrakis(methylenephosphonic acid),
ammonium salt of 1,2-diaminoethanetetrakis(methylenephosphonic acid),
aminotrimethylenephosphonic acid (ATMP),
ethylenediaminetetra(methylenephosphonic acid) (EDTMPA Solid),
phosphonobutane tricarboxylic acid, (PBTCA),
polyhydric alcohol phosphate ester (PAPE),
2-hydroxyphosphonocarboxylic acid (HPAA),
hexamethylenediaminetetra(methylenephosphonic acid) HMDTMPA, or
mixtures thereof.

Another embodiment of the invention relates to the powdered composition defined hereinabove, wherein the sequestering agent is selected from the group consisting of ethylenediaminetetraacetic acid (EDTA), nitrilotriacetic acid (NTA), phosphonates, citric acid, phosphoric acid, sulfuric acid, dipicolinic acid, sulfonic acid and boric acid.

Another embodiment of the invention relates to the powdered composition defined hereinabove, wherein the sequestering agent is selected from the group consisting of ethylenediamine tetraacetic acid (EDTA), nitrilotriacetic acid (NTA), and phosphonates.

Another embodiment of the invention relates to the powdered composition defined hereinabove, wherein the acetylating agent is an organic acid.

Another embodiment of the invention relates to the powdered composition defined hereinabove, wherein the acetylating agent is an organic acid containing at least one acyl group which is susceptible to perhydrolysis.

Another embodiment of the invention relates to the powdered composition defined hereinabove, wherein the acetylating agent is a N-acyl compound or a O-acyl compound containing an acyl radical R—CO— wherein R is an aliphatic group having from 5 to 18 carbon atoms, or an alkylaryl group having from 11 to 24 carbon atoms, with 5 to 18 carbon atoms in the alkyl chain. Preferably, R may be an aliphatic group having from 5 to 12 carbon atoms.

Another embodiment of the invention relates to the powdered composition defined hereinabove, wherein the acylating agent is tetraacetyl glycoluril (TAGU), tetraacetylethylendiamine (TAED), diacetyl dioxohexahydratriazine (DADHT), or mixtures thereof.

Another embodiment of the invention relates to the powdered composition defined hereinabove, wherein the acylating agent is acetylsalicylic acid or tetraacetylethylenediamine (TAED).

Another embodiment of the invention relates to the powdered composition defined hereinabove, wherein the solid hydrogen peroxide precursor is a persalt.

Another embodiment of the invention relates to the powdered composition defined hereinabove, wherein the persalt is sodium perborate, sodium percarbonate, ammonium percarbonate, sodium peroxyhydrate, calcium peroxide, sodium peroxide, sodium perborate monohydrate, sodium perborate tetrahydrate, sodium persulfate, potassium monopersulfate, perphosphate, magnesium peroxide, zinc peroxide, urea hydrogen peroxide, perhydrate of urea, thiourea dioxide, or mixtures thereof.

Preferably the persalt may be sodium percarbonate or ammonium percarbonate, and more preferably sodium percarbonate.

Another embodiment of the invention relates to the powdered composition defined hereinabove, wherein the pH adjusting agent is an organic acid or an inorganic acid.

Another embodiment of the invention relates to the powdered composition defined hereinabove, wherein the pH adjusting agent is sulfuric acid, sulfamic acid, citric acid, phosphoric acid, nitric acid, hydrochloric acid, glycolic acid, formic acid, acetic acid, hydrofluoric acid, nitrous acid, hydrocyanic acid, benzoic acid, carboxylic acid, lactic acid, acetic acid, oxalic acid, sulfamic acid, phosphorous acid, dipicolinic acid, urea.HCl, boric acid, or mixtures thereof. Preferably, the pH adjusting agent may be citric acid.

Another embodiment of the invention relates to the powdered composition defined hereinabove, wherein the at least one SAR inducer which is a water soluble silicate salt defining a source of silicate ions, is potassium silicate, sodium silicate, sodium metasilicate, or a mixture thereof. Preferably said water soluble silicate salt may be potassium silicate.

Another embodiment of the invention relates to the powdered composition defined hereinabove, wherein it comprises a dry, water soluble mixture of:
(i)-a) about 43.5% w/w of a sodium percarbonate as said solid hydrogen peroxide,
(i)-b) about 25% w/w a citric acid as said pH adjusting agent,
(i)-c) about 21% w/w of tetraacetylethylenediamine (TAED) as said acetylating agent;
(ii) about 10% w/w of potassium silicate as said at least one biopesticide comprising the water soluble silicate salt defining a source of silicate ions; and
(iii) about 0.5% w/w of ethylenediaminetetraacetic acid (EDTA) as said sequestering agent;
wherein (i)-a), (i)-b) and (i)-c) represent the peracetic acid precursor; and wherein when 2 g of said dry, water soluble mixture of (i)-a), (i)-b), (i)-c), (ii) and (iii) is admixed with 1000 g of water, about 100 to 250 ppm of peracetic acid (PAA), preferably 200 ppm of peracetic acid (PAA), are generated in situ at pH $7.0\pm2$, preferably $7.0\pm1.5$ and more preferably $7.0\pm1.0$.

Another embodiment of the invention relates to the powdered composition defined hereinabove, wherein it comprises a dry, water soluble mixture of:
  (i)-a) about 50% w/w of a sodium percarbonate as said solid hydrogen peroxide,
  (i)-b) about 15% w/w a citric acid as said pH adjusting agent,
  (i)-c) about 20% w/w of tetraacetylethylenediamine (TAED) as said acetylating agent;
  (ii) about 10% w/w of potassium silicate as said at least one biopesticide comprising the water soluble silicate salt defining a source of silicate ions;
  (iii) about 1% w/w of ethylenediaminetetraacetic acid (EDTA) as said sequestering agent; and
  (iv) about 4% w/w of an alpha olefin sulfonate having 12 to 18 carbon atoms;
wherein (i)-a), (i)-b) and (i)-c) represent the peracetic acid precursor; and wherein when 2 g of said dry, water soluble mixture of (i)-a), (i)-b), (i)-c), (ii), (iii) and (vi) is admixed with 1000 g of water, about 100 to 250 ppm of peracetic acid (PAA) are generated in situ at pH $8.0\pm3$.

Another embodiment of the invention relates to a method for controlling pathogens on a plant tissue of a growing plant having roots and leaves, said method comprising treating said growing plant with an aqueous solution obtained by admixing the composition or powdered composition defined hereinabove as an embodiment of the invention, the resulting aqueous solution comprising peracetic acid at a concentration and a pH which are not harmful for said plant tissue and at least one SAR inducer which is a water soluble silicate salt defining a source of silicate ions.

Another embodiment of the invention relates to the method for controlling pathogens on a plant tissue of a growing plant, as defined hereinabove, wherein said treatment is repeated according to a predetermined schedule, synergistic effect being observed once the SAR inducer which is a water soluble silicate salt defining a source of silicate ions, and the peracetic acid are respectively simultaneously present in and on the plant.

Another embodiment of the invention relates to the method for controlling pathogens on a plant tissue of a growing plant, as defined hereinabove, wherein pathogens are selected from the group consisting of viruses, bacteria, fungus, yeasts and molds. Preferably, pathogens are bacteria, and more preferably *Xanthomonas*.

Another embodiment of the invention relates to the method for controlling pathogens on a plant tissue of a growing plant, as defined hereinabove, wherein the aqueous solution comprises between about 20 ppm to about 2000 ppm of peracetic acid (PAA) and have a pH of $7.0\pm2.0$, preferably $7.0\pm1.5$ and more preferably $7.0\pm1.0$.

Another embodiment of the invention relates to the method for controlling pathogens on a plant tissue of a growing plant, as defined hereinabove, wherein the peracetic acid is generated in situ in the aqueous solution.

Another embodiment of the invention relates to the method for controlling pathogens on a plant tissue of a growing plant, as defined hereinabove, wherein said aqueous solution is sprayed onto the leaves of the growing plant, and a substrate comprising roots of said growing plant, and wherein the at least one SAR inducer which is a water soluble silicate salt defining a source of silicate ions, is absorbed by leaves and the roots of the growing plant.

Another embodiment of the invention relates to the method for controlling pathogens on a plant tissue of a growing plant, as defined hereinabove, wherein the at least one SAR inducer which is a water soluble silicate salt defining a source of silicate ions, is selected from the group consisting of:
  at least one pesticide comprising a water soluble silicate salt,
  at least one biopesticide comprising a water soluble silicate salt, and
  silica/silicate.

Another embodiment of the invention relates to the method for controlling pathogens on a plant tissue of a growing plant, as defined hereinabove, wherein the water soluble silicate salt which is defining a source of silicate ions, is potassium silicate, sodium silicate, sodium metasilicate, or a mixture thereof. Preferably, said water soluble silicate salt is potassium silicate.

Another embodiment of the invention relates to a method for controlling pathogens on a plant tissue of a growing plant having roots and leaves, said method comprising treating said growing plant with an aqueous solution resulting from the dissolution in water of the powdered composition as defined hereinabove as embodiments of the invention, the resulting aqueous solution comprising peracetic acid at a concentration and a pH which are not harmful for said plant tissue and at least one SAR inducer which is a water soluble silicate salt defining a source of silicate ions.

Another embodiment of the invention relates to the method for controlling pathogens on a plant tissue of a growing plant having roots and leaves, as defined hereinabove, wherein the aqueous solution comprises about 100 ppm, or about 200 ppm, or about 300 ppm, or about 400 ppm or 500 ppm of peracetic acid (PAA).

Another embodiment of the invention relates to the method for controlling pathogens on a plant tissue of a growing plant having roots and leaves, as defined hereinabove, wherein the growing plant is selected from the group consisting of fruit, nuts, cereals, vegetables and flowers.

Another embodiment of the invention relates to the method for controlling pathogens on a plant tissue of a growing plant having roots and leaves, as defined hereinabove, wherein the fruit is selected from the group consisting of apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive and lime.

Another embodiment of the invention relates to the method for controlling pathogens on a plant tissue of a growing plant having roots and leaves, as defined hereinabove, wherein the vegetable is artichoke, bean, beetroot, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip and peanut.

Another embodiment of the invention relates to the method for controlling pathogens on a plant tissue of a growing plant having roots and leaves, as defined hereinabove, wherein the growing plant is a cereal. Preferably, wherein the cereal is amaranth, breadnut, barley, buckwheat, canola, corn, fonio, kamut, millet, oats, *quinoa*, cattail, chia, flax, kañiwa, pitseed goosefoot, wattleseed, rice, rye, sorghum, spelt, teff, triticale, wheat, and colza.

Another embodiment of the invention relates to the method for controlling pathogens on a plant tissue of a growing plant having roots and leaves, as defined hereinabove, wherein, the plant tissue is selected from the group consisting of a leaf, a stem, a flower, a fruit, a tuber, a rhizome, a corm, a root and combinations thereof.

Another embodiment of the invention relates to the method for controlling pathogens on a plant tissue of a growing plant having roots and leaves, as defined hereinabove, wherein the nuts are selected from the group consisting of almond, beech nut, Brazil nut, butternut, cashew, chestnut, chinquapin, filbert, hickory nut, macadamia nut, pecan, walnut and pistachio.

Another embodiment of the invention relates to the method for controlling pathogens on a plant tissue of a growing plant having roots and leaves, as defined hereinabove, wherein the growing plant is turf grass or long grass.

Another embodiment of the invention relates to the method for controlling pathogens on a plant tissue of a growing plant having roots and leaves, as defined hereinabove, wherein the growing plant is tomato.

Another embodiment of the invention relates to a use of the composition or powdered composition defined hereinabove as an embodiment of the invention, for preparing an aqueous solution comprising peracetic acid at a concentration and a pH not harmful for a plant and at least one SAR inducer which is a water soluble silicate salt defining a source of silicate ions, for the treatment of a plant tissue of a growing plant in order to control pathogens thereon.

Another embodiment of the invention relates to the use defined hereinabove, wherein said treatment is repeated according to a predetermined schedule, a synergistic effect being observed once the SAR inducer which is a water soluble silicate salt defining a source of silicate ions, and the peracetic acid are respectively simultaneously present in and on the plant tissue of the growing plant.

Another embodiment of the invention relates to the use defined hereinabove, wherein pathogens are selected from the group consisting of viruses, bacteria, fungus, yeasts and molds. Preferably, pathogens are bacteria, and more preferably *Xanthomonas*.

Another embodiment of the invention relates to the use defined hereinabove, wherein the aqueous solution comprises between about 20 ppm to about 2000 ppm of peracetic acid (PAA) and has a pH of 7.0±2.0, preferably 7.0±1.5 and more preferably 7.0±1.0.

Another embodiment of the invention relates to the use defined hereinabove, wherein the peracetic acid is generated in situ in the aqueous solution.

Another embodiment of the invention relates to the use defined hereinabove, wherein said aqueous solution is sprayed onto the growing plant and a substrate of the growing plant.

Another embodiment of the invention relates to the use defined hereinabove, wherein the at least one SAR inducer which is a water soluble silicate salt defining a source of silicate ions, is absorbed by the leaves and the roots of the growing plant.

Another embodiment of the invention relates to the use defined hereinabove, wherein the at least one SAR inducer which is a water soluble silicate salt defining a source of silicate ions, is selected from the group consisting of:
at least one pesticide comprising a water soluble silicate salt,
at least one biopesticide comprising a water soluble silicate salt, and
silica/silicate.

Another embodiment of the invention relates to the use defined hereinabove, wherein the water soluble silicate salt defining a source of silicate ions is potassium silicate, sodium silicate, sodium metasilicate, or mixtures thereof. Preferably, said water soluble silicate salt is potassium silicate.

Another embodiment of the invention relates to a use of the powdered composition defined hereinabove, for preparing an aqueous solution comprising peracetic acid at a concentration and a pH not harmful for a plant and a SAR inducer which is a silicate salt defining a source of silicate ions, for the treatment of a plant tissue of a growing plant in order to control pathogens thereon.

Another embodiment of the invention relates to the use of the powdered composition defined hereinabove as embodiments of the invention, wherein said treatment is repeated according to a predetermined schedule, a synergistic effect being observed once the SAR inducer which is a water soluble silicate salt defining a source of silicate ions, and the peracetic acid are respectively simultaneously present in and on the plant tissue of the growing plant.

Another embodiment of the invention relates to the use of the powdered composition defined hereinabove, wherein the aqueous solution comprises about 100 ppm, or about 200 ppm, or about 300 ppm, or about 400 ppm or 500 ppm of peracetic acid (PAA).

Another embodiment of the invention relates to the use of the powdered composition defined hereinabove, wherein the growing plant is selected from the group consisting of fruit, nuts, cereals, vegetables and flowers.

Another embodiment of the invention relates to the use of the powdered composition defined hereinabove, wherein the fruit is selected from the group consisting of apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive and lime.

Another embodiment of the invention relates to the use of the powdered composition defined hereinabove, wherein the vegetable is artichoke, bean, beetroot, broad bean, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip and peanut.

Another embodiment of the invention relates to the use of the powdered composition defined hereinabove, wherein the growing plant is a cereal. Preferably, the cereal may be amaranth, breadnut, barley, buckwheat, canola, corn, fonio, kamut, millet, oats, *quinoa*, cattail, chia, flax, kañiwa, pitseed goosefoot, wattleseed, rice, rye, sorghum, spelt, teff, triticale, wheat, and colza.

Another embodiment of the invention relates to the use of the powdered composition defined hereinabove, wherein, the plant tissue is selected from the group consisting of a leaf, a stem, a flower, a fruit, a tuber, a rhizome, a corm, a root and combinations thereof.

Another embodiment of the invention relates to the use of the powdered composition defined hereinabove, wherein the nuts are selected from the group consisting of almond, beech nut, Brazil nut, butternut, cashew, chestnut, chinquapin, filbert, hickory nut, macadamia nut, pecan, walnut and pistachio.

Another embodiment of the invention relates to the use of the powdered composition defined hereinabove, wherein the growing plant is turf grass or long grass.

Another embodiment of the invention relates to the use of the powdered composition defined hereinabove, wherein the growing plant is tomato.

Another embodiment of the invention relates to the use of the powdered composition defined hereinabove, wherein said aqueous solution provides beneficial effects on growing plants, said beneficial effects being selected from the group consisting of controlling pathogens, protecting the plant against pathogens, promoting natural defense of the plant, providing oxygen to roots of the plant, and providing essential nutrients to the plant.

Another embodiment of the invention relates to the use of the powdered composition defined hereinabove, wherein pathogens are selected from the group consisting of viruses, bacteria, fungus, yeasts and molds. Preferably, pathogens are bacteria, and more preferably *Xanthomonas*.

Another embodiment of the invention relates to a combined use of peracetic acid and of at least one SAR inducer which is a water soluble silicate salt defining a source of silicate ions, for the treatment of a plant tissue of a growing plant in order to control pathogens thereon, said peracetic acid and SAR inducer being administered to the growing plant either separately or simultaneously, being understood that a synergistic effect being observed once said SAR inducer and said peracetic acid are respectively simultaneously present in and on the plant tissue of the growing plant.

Another embodiment of the invention relates to the combined use defined hereinabove, wherein the peracetic acid and the SAR inducer which is a water soluble silicate salt defining a source of silicate ions, are simultaneously and repetitively administered to the growing plant by spraying onto the leaves of the growing plant and onto a substrate comprising roots of said growing plant, an aqueous solution resulting from the dissolution in water of the composition defined hereinabove as an embodiment of the invention, the resulting aqueous solution comprising peracetic acid at a concentration and a pH which are not harmful for said plant tissue and at least one SAR inducer which is a water soluble silicate salt defining a source of silicate ions.

Another embodiment of the invention relates to the combined use defined hereinabove, wherein the peracetic acid and the SAR inducer which is a water soluble silicate salt defining a source of silicate ions, are simultaneously and repetitively administered to the growing plant by spraying onto the leaves of the growing plant and onto a substrate comprising roots of said growing plant, an aqueous solution resulting from the dissolution in water of the powdered composition defined hereinabove as embodiments of the invention, the resulting aqueous solution comprising peracetic acid at a concentration and a pH which are not harmful for said plant tissue and at least one SAR inducer which is a water soluble silicate salt defining a source of silicate ions.

Another embodiment of the invention relates to the combined use defined hereinabove, wherein said administration is repeated according to a predetermined schedule, a synergistic effect being observed once the SAR inducer which is a water soluble silicate salt defining a source of silicate ions, and the peracetic acid are respectively simultaneously present in and on the plant tissue of the growing plant.

Another embodiment of the invention relates to the combined use defined hereinabove, wherein the aqueous solution comprises about 100 ppm, or about 200 ppm, or about 300 ppm, or about 400 ppm or 500 ppm of peracetic acid (PAA).

Another embodiment of the invention relates to the combined use defined hereinabove, wherein the growing plant is selected from the group consisting of fruit, nuts, cereals, vegetables and flowers.

Another embodiment of the invention relates to the combined use defined hereinabove, wherein the fruit is selected from the group consisting of apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive and lime.

Another embodiment of the invention relates to the combined use defined hereinabove, wherein the vegetable is artichoke, bean, beetroot, broad bean, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip and peanut.

Another embodiment of the invention relates to the combined use defined hereinabove, wherein the growing plant is a cereal. Preferably, the cereal may be amaranth, breadnut, barley, buckwheat, canola, corn, fonio, kamut, millet, oats, *quinoa*, cattail, chia, flax, kañiwa, pitseed goosefoot, wattleseed, rice, rye, sorghum, spelt, teff, triticale, wheat, and colza.

Another embodiment of the invention relates to the combined use defined hereinabove, wherein, the plant tissue is selected from the group consisting of a leaf, a stem, a flower, a fruit, a tuber, a rhizome, a corm, a root and combinations thereof.

Another embodiment of the invention relates to the combined use defined hereinabove, wherein the nuts are selected from the group consisting of almond, beech nut, Brazil nut, butternut, cashew, chestnut, chinquapin, filbert, hickory nut, macadamia nut, pecan, walnut and pistachio.

Another embodiment of the invention relates to the combined use defined hereinabove, wherein the growing plant is turf grass or long grass.

Another embodiment of the invention relates to the combined use defined hereinabove, wherein the growing plant is tomato.

Another embodiment of the invention relates to the combined use defined hereinabove, wherein said aqueous solution provides beneficial effects on growing plants, said beneficial effects being selected from the group consisting of controlling pathogens, protecting the plant against pathogens, promoting natural defense of the plant, providing oxygen to roots of the plant, and providing essential nutrients to the plant.

Another embodiment of the invention relates to the combined use defined hereinabove, wherein pathogens are selected from the group consisting of viruses, bacteria, fungus, yeasts and molds. Preferably, pathogens are bacteria, and more preferably *Xanthomonas*.

Another embodiment of the invention relates to a kit for preparing an aqueous solution for use in controlling pathogens on a plant tissue of a growing plant, the kit comprising the water soluble mixture as defined hereinabove as an embodiment of the invention, and a user manual or instructions.

Another embodiment of the invention relates to a kit for preparing an aqueous solution for use in controlling pathogens on a plant tissue of a growing plant, the kit comprising the composition defined hereinabove as an embodiment of the invention, and a user manual or instructions.

Another embodiment of the invention relates to a kit for preparing an aqueous solution for use in controlling microbial pathogens on a plant tissue of a growing plant, the kit comprising the powdered composition as defined hereinabove as embodiment of the invention, and a user manual or instructions.

Another embodiment of the invention relates to the kits defined hereinabove wherein pathogens are selected from the group consisting of viruses, bacteria, fungus, yeasts and molds. Preferably, pathogens are bacteria, more preferably, *Xanthomonas*.

An advantage of the present invention is that it provides quick, safe, and efficient means for generating peracetic acid solutions which are safe for plant tissues and which have beneficial effects on growing plants. Another advantage of the present invention is related to an unexpected synergistic effect resulting of the combined activity of peracetic acid and at least one SAR inducer which is a water soluble silicate salt generating silicate ions.

As indicated hereinbefore, a preferred embodiment of the present invention contemplates a powdered composition which is dissolved to obtain a diluted aqueous solution prior to its utilization in controlling plants microbial pathogens.

For safety and economical reasons, in a more particularly preferred embodiment, the powdered composition would be marketed as a concentrate and the end user would dilute the concentrate with water to a use solution. The level of active components in the concentrate powdered composition and/or diluted solution will be dependent upon the intended dilution factor and desired activity in the use solution.

The aqueous solutions according to the invention can be applied to the plant tissue in a variety of techniques. For instance, the aqueous solution can be sprayed, painted, daubed, fogged, onto or into the plant, the plant hydroponic substrate, the agricultural earth (e.g. irrigation). The solution can be reapplied periodically as needed.

Another aspect of the invention pertains to commercial packages or kits for using the compositions and carrying out the methods of the invention. Kits according to the invention may be used for preparing aqueous solutions for use in controlling microbial pathogens on a plant tissue of a growing plant.

Accordingly, an additional aspect of the invention related to kits. In one embodiment, the kit includes a container (e.g. a pouch, a tablet, a bucket, etc.) comprising a powdered composition as defined herein, and a user manual or instructions. A kit of the invention may further comprise one or more of the following elements: test strips for determining peracetic levels, test strips for determining hydrogen peroxide levels, test kits for determining peracetic acid levels.

As indicated hereinbefore, in preferred embodiments, the powdered compositions according to the invention would be marketed as a concentrate to be diluted by a end user. It is also conceivable according to the invention to provide the end user with separate containers comprising individually the active components of the powdered composition according to the invention. The end user will then mix himself the active components for achieving an intended dilution factor and a desired activity.

Therefore, a kit or commercial package according to that particular embodiment would comprises a plurality of individual containers (e.g. pouch, tablet, bucket, etc.), and a user manual or instructions, the individual containers each comprising at least one of a solid hydrogen peroxide, a pH adjusting agent, and tetraacetylethylenediamine (TAED). Said individual containers (same or additional containers) further comprise at least a SAR inducer which is a water soluble silicate salt defining a source of silicate ions, more preferably a potassium silicate, and optionally sequestering agent(s).

Those skilled in the art will recognize, or be able to ascertain using no more than routine experimentation, numerous equivalents to the invention defined in the present specification. Such equivalents are considered to be within the scope of said invention.

The invention is further illustrated by the following examples, which should not be construed as further limiting.

Additional aspects, advantages and features of the present invention will become more apparent upon reading of the following non-restrictive description of preferred embodiments which are exemplary and should not be interpreted as limiting the scope of the invention.

EXAMPLES

Example 1

Formulation of a Powdered Composition According to the Invention (Hereinafter Called Ato Cide in the Following Examples)

OBJECTIVE: Formulate a powdered composition that generates peracetic acid in situ when dissolved in water The following ingredients were mixed together, according to Table 1 below:

TABLE 1

Preparation of a preferred powdered composition according to the invention and hereinafter called ATO CIDE. This powdered composition is used for the preparation of solutions used in the following examples, unless otherwise indicated.

| Compound | Quantity | Relative amount |
| --- | --- | --- |
| Coated sodium percarbonate | 4.35 kg | ~43.5% w/w |
| Citric acid (food grade) | 2.5 kg | ~25% w/w |
| Tetraacetylethylenediamine (TAED) | 2.1 kg | ~21% w/w |
| potassium silicate | 1 kg | ~10% w/w |
| Ethylenediamine tetraacetic acid (EDTA) | 50 g | ~0.5% w/w |
| TOTAL | 10 kg | 100% |

The powdered composition was prepared as follows: in a powder mixer, coated sodium percarbonate was added first, then citric acid and both compounds were mixed for at least 5 minutes. Next TAED was added and mixed for at least 5 minutes, then potassium silicate was added and mixed for at least 5 minutes. Finally, EDTA was added and mixed for 10 minutes. It is to be noted that coated sodium percarbonate is preferred. According to the present example, the sodium percarbonate is coated with a bilayer of sodium sulphate and sodium metaborate. Alternatively, it may be coated with other coating ingredients. Coating is preferred because uncoated sodium percarbonate is somewhat hygroscopic, it may begin to liquefy (i.e. dissolve in atmospheric moisture) in conditions of high relative humidity and then decompose to sodium carbonate and oxygen. As a result, sodium percarbonate would lose its potential as an oxygen donor to form peracetic acid. As a particularly preferred embodiment, a coated sodium percarbonate may be essentially coated by sparging or spraying it with heated solutions of inorganic salts that are even more hygroscopic than is sodium percarbonate itself. In this way, the coating will absorb and trap the atmospheric water that would otherwise react with the sodium percarbonate. These inorganic salts may include sodium sulphate, sodium carbonate, sodium borate or boric acid. One of these salts is applied to percarbonate crystals or granules as a heated spray in a fluidised bed. The salt solution dries onto the crystal and permanently coats it. Optionally, a second coating is then applied in the same way as the first, preferably using a different salt from that of the first coating.

The resulting mixture is a fine white powder. An aqueous 0.1% solution (e.g. 1 g in 1 L of water) has a neutral pH (7.0±1.0) and generates about 100 ppm of peracetic acid (PAA) in-situ after few hours. In the long run peracetic acid will decompose and its active concentration is reduced.

A 100 g sample was taken to the laboratory for quality control, by testing the physical structure, specific gravity, pH of a 0.2-2% solution, and the concentration of peracetic acid in a 0.2-2% solution.

A 0.2% solution (2 g per liter of water) of the powdered composition of table 1 was prepared. More particularly, the preparation of said solution comprised the following steps:

A Solution of 0.2% (2 g per 1 liter water) of the powdered composition of table 1, was prepared at room temperature.

The solution was mixed for at least 30 minutes.

Then the solution was allowed to mature for at least 4 to 24 hours for an in-situ generation of peracetic acid at neutral pH levels before using the solution.

Table 2 hereinafter illustrates the stability of ATO CIDE (i.e. the powdered mixture of Table 1) diluted in water at a concentration of 2 g per Liter at room temperature (20° C.).

| Time | Peracetic acid (powdered composition of table 1 (0.2% solution )) | Hydrogen Peroxide (powdered composition of table 1 (0.2% solution )) |
| --- | --- | --- |
| 0 hr | 15 ppm | 400 ppm |
| 1 hr, 30 min | 60 ppm | 400 ppm |
| 2 hr, 30 min | 105 ppm | 400 ppm |
| 4 hr | 135 ppm | 450 ppm |
| 21 hr | 180 ppm | 350 ppm |
| 24 hr | 200 ppm | 350 ppm |
| 28 hr | 200 ppm | 350 ppm |
| 48 hr | 150 ppm | 350 ppm |
| 54 hr | 100 ppm | 400 ppm |
| 80 hr | <15 ppm | 400 ppm |

Titrated with LaMotte Test kit for peracetic acid (code 7191-01).

The pH of the above mentioned solution of 0.2% was around pH 7 (neutral) and is the best alternative to the regular liquid peracetic acid products.

It is to be noted that the peracetic concentration remains relatively stable for a period of about 24 hours.

A 0.5% solution (5 g per liter of water) of the powdered composition of table 1 was prepared. More particularly, the preparation of said solution comprised the following steps:

A Solution of 0.5% (5 g per liter of water) of the powdered composition of table 1, was prepared at room temperature.

The solution was mixed for at least 30 minutes.

Then the solution was allowed to mature for at least 4 to 24 hours for an in situ generation of peracetic acid at neutral pH levels before using the solution.

The table 3 hereinafter illustrate the stability of the powdered composition of table 1 diluted in water at a concentration of 5 g per liter at room temperature (20° C.)

| Time | Peracetic acid (powdered composition of table 1 (0.5% solution )) | Hydrogen Peroxide (powdered composition of table 1 (0.5% solution )) |
| --- | --- | --- |
| 0 hr | 50 ppm | 1000 ppm |
| 1 hr, 30 min | 165 ppm | 1000 ppm |
| 2 hr, 30 min | 315 ppm | 1000 ppm |
| 4 hr | 390 ppm | 1050 ppm |
| 21 hr | 400 ppm | 850 ppm |
| 24 hr | 450 ppm | 850 ppm |
| 28 hr | 420 ppm | 800 ppm |
| 48 hr | 180 ppm | 800 ppm |
| 54 hr | 75 ppm | 900 ppm |
| 80 hr | <15 ppm | 850 ppm |

Titrated with LaMotte Test kit for peracetic acid (code 7191-01)

The pH of this solution is around pH 7 (neutral) and is a particularly preferred alternative to the regular liquid peracetic acid products.

It is to be noted that the peracetic concentration remains relatively stable for a period of about 24 hours.

Table 4 hereinafter compares the features of the powdered mixture of Table 1 with standard traditional commercial liquid peracetic formulations which are based on a mixture of acetic acid and hydrogen peroxide.

TABLE 4

Comparative analysis between ATO CIDE and traditional liquid peracetic acid formulations which are based on mixtures of acetic acid and hydrogen peroxide.

| Description | Powdered mixture ATO CIDE (Table 1) | Liquid Peracetic acid—Traditional liquid formulation |
| --- | --- | --- |
| Physical status | Solid | Liquid |
| Transportation | Safe | Hazardous |
| Odor | No odor | Offensive—Strong acetic acid smell |
| pH | Reacts with water to generate peracetic acid at neutral pH levels | The pH is highly acidic |
| Phytotoxicity | Not observed with used concentration | Phytotoxic |
| Handling/Employees | Safe to handle | Extremely dangerous to handle |
| Storage | Requires a limited place | Requires large and a secured space to prevent leaking |

TABLE 4-continued

Comparative analysis between ATO CIDE and traditional liquid peracetic acid formulations which are based on mixtures of acetic acid and hydrogen peroxide.

| Description | Powdered mixture ATO CIDE (Table 1) | Liquid Peracetic acid—Traditional liquid formulation |
|---|---|---|
| Chemical stability | Stable | Decomposes if exposed to heat or organic materials |
| Approximate concentration used | 0.2% (aqueous solution of 2 g/L = 20 g/10 L) | 0.4% 4 ml/L |
| Activity | 10% active (i.e. 2 g/L generates 200 ppm peracetic acid per liter of solution) | 5% active (i.e. 4 ml/L generates 200 ppm peracetic acid per liter of solution) |

The traditional liquid peracetic acid formulations are highly corrosive and reactive and are not stable for a long period of time especially if exposed to high temperatures; however, ATO CIDE is a powdered product that is much safer and stable over a longer period of time. Also, it is to be noted that in the above table, the powdered mixture ATO CIDE is 10% active while the liquid peracetic acid is 5% active.

Example 2

In-Vitro Efficiency of Ato Cide and Derivatives of the Ato Cide Formula on *Pseudomonas* and *Fusarium* Species OBJECTIVE: Laboratory study on the efficiency of ATO CIDE, derivatives of ATO CIDE formula and ingredients of ATO CIDE formula on *Pseudomonas aeruginosa* and *Fusarium* spp Material:
1) Products to be studied:
2) Bacterial strains of *Pseudomonas aeruginosa*, and *Fusarium* spp
3) Medium: PBS sterile
4) Columbia Gelose
5) PDA gelose with antibiotic Method:

Strains Preparation:

1—*Pseudomonas aeruginosa*

A cryotube of the *Pseudomonas aeruginosa* strain has been thaw and cultivated in a Petri glass (Columbia gelose) and incubated at 37° C. in a 5% $CO_2$ atmosphere. After 24 hours of incubation, Petri glasses were observed to be sure there was no contamination. A bacterial suspension of each strain was prepared at a concentration of 0.5 Mac Farland ($10^8$CFU/ml).

2—Preparation of the Strain of the *Fusarium* spp:

A cryotube of the strain of the *Fusarium* spp has been tawn and cultivated in a Petri glass (PDA gelose with antibiotic) and incubated at 37° C. under a 5% $CO_2$ atmosphere. Then Petri glasses were transferred at room temperature, and after 72 hours of incubation, said Petri glasses were observed to be sure there was no contamination. A suspension of the strain of the *Fusarium* spp was prepared (four colonies of *Fusarium* spp in 1 ml of a sterile PBS).

Preparation of Various Products to be Tested at Different Concentrations:

a. 2% concentration (2 g of the product to be tested in 100 ml of sterile PBS)
b. 5% concentration (200 mg of the product to be tested in 100 ml of sterile PBS)

More particularly, the following formula #1a to #7a and #1b to #3b were prepared. Letters <<a>> and <<b>> refer to the concentration of the products to be tested as mentioned above:

| | Potassium silicate (% w/w) | Sodium Percarbonate (% w/w) | Citric acid (% w/w) | TAED (% w/w) | EDTA (% w/w) | Sodium Perborate (% w/w) |
|---|---|---|---|---|---|---|
| Solution (2 gr/L of water) of a solid composition comprising: | | | | | | |
| #1a (K silicate) | 100 | 0 | 0 | 0 | 0 | 0 |
| #2a (sodium percarbonate, citric acid and TAED) | | 50 | 25 | 25 | 0 | 0 |
| #3a (composition of table 1 ATO CIDE formula) | 10 | 43.5 | 25 | 21 | 0.5 | 0 |
| #4a (composition of table 1 without EDTA) | 10 | 44 | 25 | 21 | 0 | 0 |
| #5a (composition of table 1 without K silicate) | 0 | 53.5 | 25 | 21 | 0.5 | 0 |
| #6a (sodium percarbonate) | 0 | 100 | 0 | 0 | 0 | 0 |
| #7a (composition of table 1 where sodium percarbonate is replaced by sodium perborate) | 10 | 0 | 25 | 21 | 0.5 | 43.5 |

-continued

| | Potassium silicate (% w/w) | Sodium Percarbonate (% w/w) | Citric acid (% w/w) | TAED (% w/w) | EDTA (% w/w) | Sodium Perborate (% w/w) |
|---|---|---|---|---|---|---|
| Solution (5 gr/L of water) of a solid composition comprising: | | | | | | |
| #1b (K silicate) | 100 | 0 | 0 | 0 | 0 | 0 |
| #2b (sodium percarbonate, citric acid and TAED) | 0 | 50 | 25 | 25 | 0 | 0 |
| #3b (composition of table 1 ATO CIDE formula) | 10 | 43.5 | 25 | 21 | 0.5 | 0 |

Execution of the Test:

Once all dilutions were made, 100 µl of each dilution was mixed with 100 µl of the formulas #1a to 7a for the *Pseudomonas* test, #1b to #3b for the *fusarium* test mentioned hereinabove, at the determined concentration. A contact time (2 min and 30 min) was observed and then grown by spreading. Plates were incubated at 37° C. in a 5% $CO_2$ atmosphere for 24 hours. Results of the above-mentioned tests were reported in the following Tables 5 to 6 hereinafter.

TABLE 5

In vitro efficiency of ATO CIDE formula, its derivatives and some of its ingredients on *Pseudomonas aeruginosa* species.

| Bacteria | Formula #2a (2 g/L) | Formula #3a (2 g/L) | Formula #6a (2 g/L) | Formula #7a (2 g/L) |
|---|---|---|---|---|
| *Pseudomonas Aeruginosa* | percarbonate, citric acid and TAED | ATO CIDE | Percarbonate | composition of ATO CIDE where percarbonate is replaced by perborate |
| After 30 minutes | Bact. | Bact. | Bact. | Bact. |

Bact. = bactericide

Results: Formulas #2a, #3a, #6a and #7a were able to control *Pseudomonas aeruginosa*, at a concentration of 2 g per L with a contact time of 30 minutes only. Also, this table 5 shows an alternative embodiment wherein the sodium percarbonate is substituted by another persalt such as for example a sodium perborate.

TABLE 6

In vitro efficiency and Synergy of ATO CIDE (formula #3b) compared to peracetic acid precursor alone (formula #2b) and the SAR inducer alone (formula #1b) on *Fusarium* spp.

| Fungi | Formula #1b (5 g/L) | Formula #2b (5 g/L) | Formula #3b (5 g/L) |
|---|---|---|---|
| *Fusarium* spp | (K silicate) | (percarbonate, citric acid and TAED) | ATO CIDE |
| After 2 minutes | Growth +++ | Growth + | No growth |

Results: ATO CIDE (formula #3b) was able to inhibit completely the growth of *Fusarium* spp at a concentration of 5 g per L with a contact time of 2 minutes only. The peracetic acid precursor alone (formula #2b) was not able to inhibit completely the growth of *Fusarium* spp at a concentration of 5 g per L with a contact time of 2 minutes only. The SAR inducer alone (formula #1b) did not control at all the growth of *Fusarium* spp at a concentration of 5 g per L with a contact time of 2 minutes only. Table 6 demonstrates the efficiency of ATO CIDE formula and thus a synergy between the Peracetic acid precursor components and the SAR inducer component of the ATO CIDE formula.

Example 3

In Vivo Efficiency of Ato Cide Against *Xanthomonas* on Tomatoes and Proven Synergy Between the Peracetic Acid Precursor and the Sar Elicitor Components of the Ato Cide Formula Objective The efficacy and synergy of an aqueous solution obtained from the powdered composition of table 1 was determined concerning bacterial spot (*Xanthomonas perforans*) on growing plant producing tomatoes in a greenhouse in Florida.

The target endpoint evaluations were the following:

Assessment for disease severity (to be conducted 7 days after treatment (DAT).

Crop tolerance (phytotoxicity).

Tomato seedlings (5-6 week-old seedling stage; approx. 4-6 true leaves) raised from surface-sterilized seeds in a growth room. Seedlings may have been treated with imidacloprid to control the proliferation of white flies and the viral pathogens they may carry.

The environmental conditions (air, temperature, relative humidity, leaf- and soil wetness, etc) of the growth room were made conducive to the development of bacterial spot in the tomato seedlings.

Inoculation:

The inoculation was made with copper-tolerant field strains of *Xanthomonans perforans* using standard inoculation methods and techniques Tomato plants were configured in a completely randomized design prior to inoculation. Each treatment replicate was represented by a single plant, and there was a minimum of ten (10) replicates per treatment. Plants were spaced at 7-inch intervals and maintained in experimental conditions until the conclusion of the trial. A linear mixed model was used for statistical analysis.

Treatment List:

Treatments 1 to 22 were carried out. Those treatments are identified by acronyms TRT 1 to TRT 22. Applications were targeted at preventative timings (i.e. prior to disease symptoms). In the following list, the expression Ato Cide corresponds to the formulation of table 1 hereinabove.

TRT 1: Untreated, Uninoculated control.

TRT 2: Untreated, Inoculated control (sprayed with water only).

TRT 3: Ato-Cide 1 g/L of water (0.14 oz/gal)=100 ppm of active peracetic acid applied as foliar spray 7 days before inoculation.

TRT 4: Ato Cide 2 g/L of water (0.28 oz/gal)=200 ppm of active peracetic acid applied as foliar spray 7 days before inoculation.

TRT 5: Ato Cide 5 g/L of water (0.68 oz/gal)=500 ppm of active peracetic acid applied as foliar spray 7 days before inoculation.

TRT 6: Ato Cide 10 g/L of water (1.4 oz/gal)=1000 ppm of active peracetic acid applied as foliar spray 7 days before inoculation.

TRT 7: Ato Cide 20 g/L of water (2.8 oz/gal)=2000 ppm of active peracetic acid applied as foliar spray 7 days before inoculation.

TRT 8: Ato Cide 1 g/L of water (0.14 oz/gal)=100 ppm of active peracetic acid applied as foliar spray 7 days before inoculation, then 15 minutes before inoculation on the day of inoculation, then every 3-4 days thereafter for the duration of the trial.

TRT 9: Ato Cide 2 g/L of water (0.28 oz/gal)=200 ppm of active peracetic acid applied as foliar spray 7 days before inoculation, then 15 minutes before inoculation on the day of inoculation, then every 3-4 days thereafter for the duration of the trial.

TRT 10: Ato Cide 5 g/L of water (0.68 oz/gal)=500 ppm of active peracetic acid applied as foliar spray 7 days before inoculation, then 15 minutes before inoculation on the day of inoculation, then every 3-4 days thereafter for the duration of the trial.

TRT 11: Ato Cide 10 g/L of water (1.4 oz/gal)=1000 ppm of active peracetic acid applied as foliar spray 7 days before inoculation, then 15 minutes before inoculation on the day of inoculation, then every 3-4 days thereafter for the duration of the trial.

TRT 12: Ato Cide 20 g/L of water (2.8 oz/gal)=2000 ppm of active peracetic acid applied as foliar spray 7 days before inoculation, then 15 minutes before inoculation on the day of inoculation, then every 3-4 days thereafter for the duration of the trial.

TRT 13: Ato Cide 1 g/L of water (0.14 oz/gal)=100 ppm of active peracetic acid applied as foliar spray 15 minutes before inoculation on the day of inoculation, then every 3-4 days thereafter for the duration of the trial.

TRT 14: Ato Cide 2 g/L of water (0.28 oz/gal)=200 ppm of active peracetic acid applied as foliar spray 15 minutes before inoculation on the day of inoculation, then every 3-4 days thereafter for the duration of the trial.

TRT 15: Ato Cide 5 g/L of water (0.68 oz/gal)=500 ppm of active peracetic acid applied as foliar spray 15 minutes before inoculation on the day of inoculation, then every 3-4 days thereafter for the duration of the trial.

TRT 16: Ato Cide 10 g/L of water (1.4 oz/gal)=1000 ppm of active peracetic acid applied as foliar spray 15 minutes before inoculation on the day of inoculation, then every 3-4 days thereafter for the duration of the trial.

TRT 17: Ato Cide 20 g/L of water (2.8 oz/gal)=2000 ppm of active peracetic acid applied as foliar spray 15 minutes before inoculation on the day of inoculation, then every 3-4 days thereafter for the duration of the trial.

TRT 18: Kocide 3000 at 0.75 lbs/acre+Penncozeb at 0.5 lbs/acres applied as foliar spray 3-4 hours prior to inoculation.

TRT 19: Kocide 3000 at 0.75 lbs/acre applied as foliar spray 3-4 hours prior to inoculation.

TRT 20: Actigard 50WG applied as a foliar spray at the rate of 0.33 oz/acre 7 days before inoculation.

TRT 21: Aqueous solution containing 0.2 gr of a powdered potassium silicate (Kasil SS) per liter of water (i.e. 0.03 oz/gal), applied as a foliar spray 7 day before inoculation. In this case, the aqueous solution of potassium silicate obtained represents an aqueous solution of a SAR (systemic acquired resistance) elicitor or inducer.

TRT 22: Aqueous solution containing 1.8 gr of a powdered peracetic acid precursor per liter of water (0.27 oz/gal) applied as a foliar spray 15 minutes before inoculation and then every 3-4 days thereafter for the duration of the treatment. In this case, the powdered peracetic acid precursor is a mixture of a coated sodium percarbonate+TAED+citric acid.

It is to be noted that in TRT 18 to TRT 20, Kocide or Actigard were used. Kocide [3000] is a commercial grower standard in the management of crop plant bacterial pathogens against which Ato Cide is compared and contrasted. Kocide 3000 consists of 46% copper hydroxide by weight, which is equivalent to 30% elemental copper by weight. Actigard 50WG ("WG"="wettable granules") consists of 50% acibenzolar-5-methyl (=benzo (1,2,3) thiadiazole-7-carbothioic acid-5-methyl ester) by weight. This compound is a systemic acquired resistance (SAR) inducer or elicitor. It is a commercial grower standard against which the efficacy of Ato Cide and its constituents (namely, a mixture including peracetic acid and potassium silicate) are compared and contrasted.

Product Mixing:

Each solution prepared was allowed to settle for 24 hours before starting to spray the foliage. Optimal peracetic acid concentration was attained by about 24 hours after mixing was completed. Peracetic solutions were stable for up to 72 hours after mixing.

Efficacy Assessments:

The disease severity (DS) was determined according to the following protocol. At the end of the trial, leaf area was measured and the number of lesions on it were count in order to compare the number of lesions per surface area measured.

The incidence of bacterial spot on greenhouse tomato are reported in the following tables 7 and 8.

TABLE 7

Efficiency of ATO CIDE formula and phytotoxicity of treatments vs bacterial spot on greenhouse tomato in Florida (Spray interval range 4-7 days)

| Treatment | | Application schedule | # lesions/plants 9DAI | % disease control vs untreated 9DAI | % Dosage |
|---|---|---|---|---|---|
| TRT 2 | Untreated | N/A | 113 | 0 | 0 |
| TRT 3 | 0.15 oz/gal Ato Cide | 7DBI | 57 | 50 | 0 |
| TRT 4 | 0.3 oz/gal Ato Cide | 7 DBI | 33 | 71 | 0 |
| TRT 5 | 0.7 oz/gal Ato Cide | 7 DBI | 26 | 77 | 0 |
| TRT 6 | 1.5 oz/gal Ato Cide | 7 DBI | 15 | 87 | 2 |
| TRT 7 | 3.0 oz/gal Ato Cide | 7 DBI | 8 | 93 | 8 |
| TRT 8 | 0.15 oz/gal Ato Cide | 7 DBI, 15 MBI, EVERY 4 DAI | 7 | 94 | 0 |

TABLE 7-continued

Efficiency of ATO CIDE formula and phytotoxicity of
treatments vs bacterial spot on greenhouse tomato in Florida
(Spray interval range 4-7 days)

| | Treatment | Application schedule | # lesions/plants 9DAI | % disease control vs untreated 9DAI | % Dosage |
|---|---|---|---|---|---|
| TRT 9 | 0.3 oz/gal Ato Cide | 7 DBI, 15 MBI, EVERY 4 DAI | 3 | 97 | 0 |
| TRT 10 | 0.7 oz/gal Ato Cide | 7 DBI, 15 MBI, EVERY 4 DAI | 1 | 99 | 0 |
| TRT 11 | 1.5 oz/gal Ato Cide | 7 DBI, 15 MBI, EVERY 4 DAI | 0 | 100 | 1 |
| TRT 12 | 3.0 oz/gal Ato Cide | 7 DBI, 15 MBI, EVERY 4 DAI | 0 | 100 | 7 |
| TRT 13 | 0.15 oz/gal Ato Cide | 15 MBI, EVERY 4 DAI | 20 | 82 | 0 |
| TRT 14 | 0.3 oz/gal Ato Cide | 15 MBI, EVERY 4 DAI | 6 | 95 | 0 |
| TRT 15 | 0.7 oz/gal Ato Cide | 15 MBI, EVERY 4 DAI | 6 | 95 | 0 |
| TRT 16 | 1.5 oz/gal Ato Cide | 15 MBI, EVERY 4 DAI | 4 | 96 | 0 |
| TRT 17 | 3.0 oz/gal Ato Cide | 15 MBI, EVERY 4 DAI | 2 | 98 | 1 |
| TRT 18 | 0.75 lbs/ac Kocide | 4 HBI, EVERY 4 DAI | 13 | 88 | 0 |
| | 3000 + 0.5 lb/ac Penncozeb | DAI | | | |
| TRT 19 | 0.75 lbs/ac Kocide 3000 | 4 HBI, EVERY 4 DAI | 75 | 34 | 0 |
| TRT 20 | 0.33 oz/ac Actigard 50WG | 7 DBI | 12 | 89 | 0 |
| TRT 21 | 0.03 oz/gal SAR elicitor | 7 DBI | 57 | 50 | 0 |
| TRT 22 | 0.27 oz/gal PAA precursor | 15 MBI, EVERY 4 DAI | 21 | 81 | 0 |

MBI = minutes before inoculation
HBI = hours before inoculation
DBI = days before inoculation
DAI = days after inoculation
Formula of:

$$\% \text{ disease control vs untreated} = 1 - \frac{\text{\# of lesions/plants in a treatment}}{113 \left( \frac{\text{\# of lesions/plants}}{\text{in TRT \#2}} \right)} \times 100$$

Results: ATO CIDE at used concentrations was very efficient in controlling bacterial spot in greenhouse tomatoes. ATO CIDE at used concentrations was not phytotoxic to greenhouse tomatoes in Florida.

TABLE 8

Efficiency of ATO CIDE and proven synergy between the peracetic acid precursor and the SAR elicitor components of the ATO CIDE formula in controlling bacterial spot in greenhouse tomatoes in Florida.

| | Treatment | Dosage (oz/gal) | Application schedule | # lesions/plants | % disease control vs untreated (9 DAI) |
|---|---|---|---|---|---|
| TRT 2 | Untreated inoculated | N/A | N/A | 113 | 0 |
| TRT 21 | SAR inducer alone | 0.03 oz/gal SAR elicitor | 7 days before inoculation | 57 | 50 |
| TRT 22 | Peracetic acid precursor alone | 0.27 oz/gal PAA precursor | 15 minutes before inoculation, then every 4 days after application | 21 | 81 |
| TRT 9 | Ato Cide formula. It is the combination of TRT 21 and TRT 22 Ato Cide (0.3 oz/gal) = TRT 21 (0.03 oz/gal) + TRT 22 (0.27 oz/gal) | 0.3 oz/gal Ato Cide | 7 days before inoculation, then 15 minutes before inoculation, then every 4 days after application | 3 | 97 |

DAI = days after inoculation
Formula of :

$$\% \text{ disease control vs untreated} = 1 - \frac{\text{\# of lesions/plants in a treatment}}{113 \left( \frac{\text{\# of lesions/plants}}{\text{in TRT \#2}} \right)} \times 100$$

Results: Table 8 proves the synergy between the peracetic acid generated from the peracetic precursor and the SAR inducer components of the ATO CIDE formula in controlling bacterial spot in greenhouse tomatoes in Florida. It is to be noted that in the untreated inoculated treatment (TRT 2), 113 lesions/plants were observed after 9 days of inoculation. In the SAR inducer treatment (TRT 21), 57 lesions/plants were observed after 9 days of inoculation. In the peracetic acid precursor treatment (TRT 22), 21 lesions/plants were observed after 9 days of inoculation. In the ATO CIDE treatment (TRT 9), only 3 lesions/plants were observed after 9 days of inoculation.

This experiment proves the unexpected synergy between peracetic acid and the SAR inducer in the formula of ATO CIDE because the efficiency of ATO CIDE, which reduced the number of lesions/plants from 113 to only 3 lesions, is far greater than what can be expected from the combined efficiencies of the SAR inducer (TRT 21=57 lesions) and peracetic acid precursor treatments (TRT 22=21 lesions).

Example 4

Laboratory Efficiency of Ato Cide Against Different Pathogenic Bacteria

Objective: Study of the bactericidal effect of the ATO CIDE (Batch product: 041109-1)
Material:
1) The powdered composition of table 1:
2) Bacterial strains
3) Medium: PBS sterile
4) Columbia Gelose Method:
Preparation of the Bacterial Strains:
A cryotube of each strain of:
*Salmonella* spp;
*Listeria monocytogenes;*
*Escherichia coli* O157 H7;
*Bacillus subtilus* ATCC 6633;
*Klebsiella pneumoniae* ATCC 13883;
*Staphylococcus aureus* ATCC 33591
was thawed and grown in a Petri glass (Columbia gelose) and incubated at 37° C. in a 5% $CO_2$ atmosphere. After 24 h of incubation, the Petri glasses were observed to be sure there was no contamination. A suspension of each bacterial strain was prepared at a concentration of 0.5 Mac Farland ($10^8$ CFU/ml), Preparation of Solution with Powdered Composition of Table 1, at Various Concentrations:
a. 0.08% concentration (80 mg of the powdered composition of table 1 in 100 ml of sterile PBS)
b. 0.2% concentration (200 mg of the powdered composition of table 1 in 100 ml of sterile PBS)
c. 0.5% concentration (500 mg of the powdered composition of table 1 in 100 ml sterile PBS)

Execution of the Test:
Once all dilutions were made, the bacteria were exposed to the ATO CIDE product at concentrations and contact time as described in table 10. Then growing by spreading was carried out. Plates were incubated at 37° C. in a 5% $CO_2$ atmosphere for 24 hours. Results of the above-mentioned tests were reported in the following Table 9 hereinafter.

TABLE 9

Efficiency of ATO CIDE formula on different pathogenic bacteria

| Micro-organisms | Initial Population (CFU/ml) for a standard MF 0.5 | Contact time | Populaion (CFU/ml) after contact at 0.08% | Log reduction | Population (CFU/ml) after contact at 0.2% | Log reduction | Population (CFU/ml) after contact at 0.5% | Log reduction |
|---|---|---|---|---|---|---|---|---|
| *Salmonella* spp | $8.10^6$ | After 2 mn | <2 | 6.6 | <2 | 6.6 | — | — |
| | | After 30 mn | <2 | 6.6 | <2 | 6.6 | <2 | 6.6 |
| *Listeria monocytogenes* | $9.10^6$ | After 2 mn | <2 | 6.7 | <2 | 6.7 | — | — |
| | | After 30 mn | <2 | 6.7 | <2 | 6.7 | <2 | 6.7 |
| *Escherichia coli* O157 H7 | $2.10^7$ | After 2 mn | <2 | 7 | <2 | 7 | <2 | 7 |
| | | After 30 mn | <2 | 7 | <2 | 7 | <2 | 7 |
| *Bacillus subtilus* ATCC 6633 | $6.2.10^6$ | After 2 mn | 870 | 3.9 | 680 | >3.9 | 870 | 3.9 |
| | | After 30 mn | 560 | 4 | 360 | >4.2 | 360 | >4.2 |
| *Klebsiella pneumoniae* ATCC 13883 | $7.10^6$ | After 2 mn | <2 | 6.5 | <2 | 6.5 | <2 | 6.5 |
| | | After 30 mn | <2 | 6.5 | <2 | 6.5 | <2 | 6.5 |
| *Staphylococcus aureus* ATCC 33591 | $8.10^6$ | After 2 mn | <2 | 6.6 | <2 | 6.6 | <2 | 6.6 |
| | | After 30 mn | <2 | 6.6 | <2 | 6.6 | <2 | 6.6 |

Results: It is to be noted that solutions prepared according to the invention are efficient against various bacterial strains. ATO CIDE at concentrations as low as 0.08% and 0.2% can kill most known pathogenic bacteria in 2 minutes contact time.

The following examples will show that ATO CIDE is efficient at killing bacteria and fungus on a plurality of growing plants.

Example 5

Efficacy of Ato Cide in Controlling *Xanthomonas* Leaf Spot on Greenhouse Romaine Lettuce in Quebec Canada Procedure Romaine lettuce was sown in a randomised block design with four replicates. Each plot consisted of one seedling tray. There were a total of twenty plots.

Five different treatments were used:
untreated control
Ato Cide at 50 ppm PAA (i.e. an aqueous solution of 0.5 g/L of the powdered composition of table 1 applied at a rate of 0.1 kg/ha)
Ato Cide at 100 ppm PAA (i.e. an aqueous solution of 1 g/L of the powdered composition of table 1 applied at a rate of 0.2 kg/ha)
Ato Cide at 200 ppm PAA (i.e. an aqueous solution of 2 g/L of the powdered composition of table 1 applied at a rate of 0.4 kg/ha)
Copper hydroxide 50% at 4.5 kg/ha copper Four product applications were made. Intervals between applications were 3 days, 8 days and 4 days respectively.

Observations (disease symptoms, and leaf injury due to product) were made at the following intervals:
Nine days after the first application.
Eight days after the second application.
Four days after the third application.
Three days after the fourth application.
The centre row of each plot was assessed for:
Leaf burn due to product [phytotoxicity]—visual.
Disease incidence (percentage of infected plants per plot)—measurement.
Disease severity (total diameter of disease spots per plot)—measurement.

Raw data were transformed using conservative statistical methods that do pairwise comparisons.

Results:
No phytotoxicity was observed at any dosage. Ato Cide at a minimum of 100 ppm PAA was required to control disease significantly relative to the untreated controls. Ato Cide at 100 ppm PAA reduced disease incidence by 85-95% relative to the untreated control as opposed to copper hydroxide, which only reduced disease incidence by 40% at best relative to the untreated control.

Example 6

Efficacy of Ato Cide in Controlling *Xanthomonas* Leaf Spot on Greenhouse Head Lettuce Auburn Alabama Procedure
Iceberg lettuce was sown in a randomised block design with ten replicates. Each plot consisted of one potted plant. There were a total of eighty plots.
Eight different treatments were used:
untreated uninoculated control
untreated inoculated control
Ato Cide at 50 ppm PAA (i.e. an aqueous solution of 0.5 g/L of the powdered composition of table 1)
Ato Cide at 100 ppm PAA (i.e. an aqueous solution of 1 g/L of the powdered composition of table 1)
Ato Cide at 200 ppm PAA (i.e. an aqueous solution of 2 g/L of the powdered composition of table 1)
Ato Cide at 500 ppm PAA (i.e. an aqueous solution of 5 g/L of the powdered composition of table 1)
Ato Cide at 1000 ppm PAA (i.e. an aqueous solution of 10 g/L of the powdered composition of table 1)
Copper hydroxide 46% at 0.5-0.75 kg/ha copper.

At present, there is no reliable commercial grower standard available for the management of bacterial pathogens (e.g. *Xanthomonas*) infesting lettuce. Essentially producers use copper salts (such as hydroxide) or rarely antibiotics such as streptomycin, oxytetracycline or kasugamycin. The preferred choice is copper, which has been known to cause leaf burn or phytotoxicity in lettuce. Copper provides a protective coating on plant surfaces against bacterial invasion and infection. It may also poison pathogen metabolism.

TABLE 10

EFFICACY OF ATO CIDE IN CONTROLLING *XANTHOMONAS* LEAF SPOT ON GREENHOUSE ROMAINE LETTUCE IN QUEBEC, CANADA
INCIDENCE OF BACTERIAL LEAF SPOT ON GREENHOUSE LETTUCE SPRAY
INTERVAL RANGE: 3-9 DAYS

| Treatment | % of leaves diseased | | | | | % disease control vs untreated | | | | |
|---|---|---|---|---|---|---|---|---|---|---|
| Date | 03 Jun. 2010 | 10 Jun. 2010 | 18 Jun. 2010 | 02 Jul. 2010 | 09 Jul. 2010 | 03 Jun. 2010 | 10 Jun. 2010 | 18 Jun. 2010 | 02 Jul. 2010 | 09 Jul. 2010 |
| Untreated | 33 | 27 | 40 | 42 | 40 | 0 | 0 | 0 | 0 | 0 |
| 0.1 kg/ha Ato Cide | 17 | 25 | 25 | 13 | 15 | 48 | 7 | 38 | 69 | 63 |
| 0.2 kg/ha Ato Cide | 23 | 31 | 33 | 2 | 6 | 30 | −15 | 18 | 95 | 85 |
| 0.4 kg/ha Ato Cide | 19 | 25 | 27 | 13 | 15 | 42 | 7 | 33 | 69 | 63 |
| 4.5 kg/ha copper hydroxide 50% | 32 | 33 | 31 | 25 | 25 | 3 | −22 | 23 | 40 | 38 |

LEGEND: kg = kilograms; ha = hectares

The purpose of using copper hydroxide in this trial was to compare and contrast the relative degrees of phytotoxicity (if any), as well as disease control (efficacy), with Ato Cide.

Product applications were made every 3-4 days starting at 3 days post-inoculation until harvest.

Observations (disease symptoms, plant vigour and leaf injury due to product) were made one week before harvest.

Each plot was assessed for:
Leaf burn due to product [phytotoxicity]—visual.
Disease incidence (percentage of infected plants per plot)—measurement.
Disease severity (relative intensity of infection on sample leaf from each plot on a scale of 1-9, with 9 being the worst)—measurement.
Plant vigour (on a scale of 1-5, with 5 being the best)—visual.

TABLE 11

Efficiency of ATO CIDE in controlling the percentage of disease caused by bacterial leaf spot on greenhouse lettuce in Auburn Alabama with different concentrations of ATO CIDE. SEVERITY OF BACTERIAL LEAF SPOT ON GREENHOUSE LETTUCE SPRAY INTERVAL RANGE: 3-4 DAYS

| Treatment | % of leaves diseased | % disease control vs Untreated |
|---|---|---|
| Untreated | 33 | 0 |
| 0.5 g/L Ato Cide | 15 | 55 |
| 1 g/L Ato Cide | 9 | 73 |
| 2 g/L Ato Cide | 8 | 76 |
| 5 g/L Ato Cide | 9 | 73 |
| 10 g/L Ato Cide | 5 | 85 |
| 0.5-0.75 kg/ha copper hydroxide 46% | 5 | 85 |

LEGEND: g = grams; L = liters; kg = kilograms; ha = hectares.

Raw data were transformed using conservative statistical methods that do pairwise comparisons.

Results:

No phytotoxicity was observed at any Ato Cide dosage. Ato Cide at 1000 ppm PAA matched copper hydroxide in disease severity reduction: 85% relative to that of the untreated inoculated control. Ato Cide at 1000 ppm PAA matched copper hydroxide in reducing disease severity to a rating of 1.5 from 8.0 for the untreated inoculated control. The vigour of plants treated with Ato Cide at 1000 ppm PAA and copper hydroxide (4.8) exceeded that of untreated uninoculated controls (4.5).

Example 7

Efficacy of Ato Cide in Controlling Pseudomonas Angular Leaf Spot on Greenhouse Cucumber in Auburn Alabama Procedure Cucumber was sown in a randomised block design with ten replicates. Each plot consisted of one potted plant. There were a total of seventy plots.

Seven different treatments were used:
untreated uninoculated control
untreated inoculated control
Ato Cide at 200 ppm PAA (i.e. an aqueous solution of 2 g/L of the powdered composition of table 1)
Ato Cide at 500 ppm PAA (i.e. an aqueous solution of 5 g/L of the powdered composition of table 1)
Ato Cide at 1000 ppm PAA (i.e. an aqueous solution of 10 g/L of the powdered composition of table 1)
Ato Cide at 2000 ppm PAA (i.e. an aqueous solution of 20 g/L of the powdered composition of table 1)
Copper hydroxide 46% at 0.5-1.25 kg/ha copper. It is to be noted that copper hydroxide is approved for the management of bacterial pathogens infesting certain hardier crop plant species. In the case of cucumber, there are virtually no agents known to control Pseudomonas infections effectively. Growers resort to copper salts since there is no alternatives. The purpose of using copper hydroxide in this trial was to compare and contrast the relative degrees of phytotoxicity (if any), as well as disease control (efficacy), with Ato Cide.

Product applications were made every 3-4 days starting at 3 days post-inoculation until harvest.

Observations (disease symptoms, plant vigour and leaf injury due to product) were made one week before harvest.

Each plot was assessed for:
Leaf burn due to product [phytotoxicity]—visual.
Disease incidence (number of disease spots per leaf)—measurement.
Disease severity (relative intensity of infection on sample leaf from each plot on a scale of 1-9, with 9 being the worst)—measurement.
Plant vigour (on a scale of 1-5, with 5 being the best)—visual.

TABLE 12

Efficiency of ATO CIDE in controlling the percentage of disease caused by angular leaf spot on greenhouse cucumber in Auburn Alabama with different concentrations of ATO CIDE. SEVERITY OF ANGULAR LEAF SPOT ON GREENHOUSE CUCUMBER SPRAY INTERVAL RANGE: 3-4 DAYS

| Treatment | % of leaves diseased | % disease control vs untreated |
|---|---|---|
| Untreated | 26 | 0 |
| 2 g/L Ato Cide | 17 | 35 |
| 5 g/L Ato Cide | 8 | 69 |
| 10 g/L Ato Cide | 5 | 81 |
| 20 g/L Ato Cide | 3 | 88 |
| 0.5-1.25 kg/ha copper hydroxide 46% | 5 | 81 |

LEGEND: g = grams; L = liters; kg = kilograms; ha = hectares.

Raw data were transformed using conservative statistical methods that do pairwise comparisons.

Results:

No phytotoxicity was observed at any Ato Cide dosage. Ato Cide at 1000 ppm PAA (10 gr/liter) matched copper hydroxide in disease severity reduction: 81% relative to that of the untreated inoculated control. Ato Cide at 2000 ppm PAA (20 gr/liter) reduced disease severity by 88% relative to that of the untreated inoculated control. Ato Cide at 1000 ppm PAA (10 gr/liter) matched copper hydroxide in reducing disease severity to a rating of 1.5 from 8.0 for the untreated inoculated control.

The vigour of plants treated with Ato Cide at 2000 ppm PAA (20 gr/liter) and copper hydroxide matched that of untreated uninoculated controls (~4).

Example 8

Efficacy of Ato Cide in Controlling Xanthomonas Spot on Greenhouse Tomato in Quebec Canada Procedure Tomato was sown in a randomised block design with four replicates. Each plot consisted of five plants. There were a total of twenty plots.

Five different treatments were used:
untreated control
Ato Cide at 50 ppm PAA (i.e. an aqueous solution of 0.5 g/L of the powdered composition of table 1 applied at a rate of 0.18 kg/ha)
Ato Cide at 100 ppm PAA (i.e. an aqueous solution of 1 g/L of the powdered composition of table 1 applied at a rate of 0.35 kg/ha)
Ato Cide at 200 ppm PAA (i.e. an aqueous solution of 2 g/L of the powdered composition of table 1 applied at a rate of 0.7 kg/ha)
Copper hydroxide 50% at 4.5 kg/ha+chlorothalonil 1 kg/ha Seven product applications were made. Intervals between applications were seven-, two-, five-, three-, five- and seven days respectively.

Observations (disease symptoms, and leaf injury due to product) were made at the following intervals:
Four days after the first application.
Eight days after the second application.
Four days after the third application.
Three days after the fourth application.

The centre leaves of each plot was assessed for:
Leaf burn due to product [phytotoxicity]—visual.
Disease incidence (percentage of infected plants per plot)—measurement.
Disease severity (total diameter of disease spots per plot)—measurement.

TABLE 13

Efficiency of ATO CIDE in controlling bacterial leaf spot in greenhouse tomato in Quebec Canada with different concentration of ATO CIDE.
SEVERITY OF BACTERIAL SPOT ON GREENHOUSE TOMATO SPRAY INTERVAL RANGE: 3-8 DAYS

| Treatment | total size disease spots (mm) | | % disease control vs untreated | |
|---|---|---|---|---|
| | July 27 | August 8 | July 27 | August 8 |
| Untreated | 65 | 516 | 0 | 0 |
| 0.18 kg/ha Ato Cide | 3 | 269 | 95 | 48 |
| 0.35 kg/ha Ato Cide | 18 | 276 | 72 | 47 |
| 0.7 kg/ha Ato Cide | 11 | 127 | 83 | 75 |
| 4.5 kg/ha copper hydroxide 50% 1 kg/ha chlorothalonil | 8 | 139 | 88 | 73 |

LEGEND: kg = kilograms; ha = hectares; mm = millimeters.

Raw data were transformed using conservative statistical methods that do pairwise comparisons.

Results:
No phytotoxicity was observed at any dosage. Ato Cide at 200 ppm PAA (0.7 kg/ha) reduced disease severity by 75-85% relative to the untreated control as opposed to copper hydroxide+chlorothalonil which reduced disease severity by 75-90% but only at far higher concentrations than those of Ato Cide.

Copper hydroxide is approved for the treatment of bacterial pathogens like *Xanthomonas* on tomato, and as such growers may use it as a commercial standard even though its efficacy here is marginal, and there is the risk of phytotoxicity to tomato leaves. The purpose of using copper hydroxide in this trial was to compare and contrast the relative degrees of phytotoxicity (if any), as well as disease control (efficacy), with Ato Cide.

Chlorothalonil (2,4,5,6-tetrachloroisophthalonitrile) has not been shown to be efficacious in managing plant bacterial disease but it is a standard treatment for a variety of fungal pathogens. It has a multi-site mode of action and is non-systemic. It binds to glutathione in fungal cells and prevents them from activating vital enzymes. Its purpose here was primarily for maintenance, that is, to suppress fungal pathogens that might have interfered with the experiment either by outcompeting the *Xanthomonas* bacteria or else themselves damaging or killing the host plants.

Example 9

Efficacy of Ato Cide in Controlling *Fusarium* Patch on Turfgrass in British Columbia Canada Procedure:
Creeping bentgrass was naturally inoculated with *Fusarium* patch disease. Four plots were assessed, and each plot was four square meters of mature turf. Four replicates were used per treatment. Six different treatments were used:
untreated control sprayed with water.
Ato Cide at 200 ppm PAA (i.e. an aqueous solution of 2 g/L of the powdered composition of table 1 applied at a rate of 2 kg/ha).
Ato Cide at 500 ppm PAA (i.e. an aqueous solution of 5 g/L of the powdered composition of table 1 applied at a rate of 5 kg/ha).
Ato Cide at 750 ppm PAA (i.e. an aqueous solution of 7.5 g/L of the powdered composition of table 1 applied at a rate of 7.5 kg/ha).
Ato Cide at 1000 ppm PAA (i.e. an aqueous solution of 10 g/L of the powdered composition of table 1 applied at a rate of 10 kg/ha).
Azoxystrobin at six grams per one hundred square meters. Azoxystrobin is a broad-spectrum fungicide with a single-site mode of action: it binds very tightly to the Qo site of Complex III in the mitochondrial electron transport chain of fungal pathogens. Thus the disease pest is prevented from generating ATP, so it dies for lack of metabolic energy. Azoxystrobin is itself extracted from certain Eastern European mushrooms reputed for their resistance to disease induced by other fungi. Azoxystrobin, marketed under the brand name of Heritage, is one of the commercial standards used in the management of *Fusarium* Patch disease on turf grass. It was against this reference that the efficacy of Ato Cide in controlling this pathogen was compared and contrasted.

Spray volume was one thousand liters per hectare. Three product applications were made. The interval between applications was 14 days.

Observations (disease symptoms, leaf damage due to product, and grass vigour) were made at the following intervals:
Immediately prior to each application.
Nine days after the last (third) application.
Sixty days after the last (third) application.
Ninety days after the last (third) application.

Each plot was assessed for:
Leaf burn due to product [phytotoxicity]—visual; on a percentage scale.
Disease incidence (number of disease patches)—measurement.
Disease severity—visual; relative percentage of total turfgrass area that was diseased.
Grass vigour—visual; on a scale of 1-9.

TABLE 14

Efficiency and percentage disease control of *Fusarium* Patch on Turfgrass with different concentrations of ATO CIDE. SEVERITY OF *FUSARIUM* PATCH ON TURFGRASS SPRAY INTERVAL RANGE: 14 DAYS (TOTAL 3 APPLICATIONS)

| Treatment | mean # disease spots/plot | | % disease control vs untreated | |
|---|---|---|---|---|
| | Winter | Spring | Winter | Spring |
| Untreated | 13 | 12 | 0 | 0 |
| 2 kg/ha Ato Cide | 10 | 8 | 23 | 33 |
| 5 kg/ha Ato Cide | 2 | 5 | 85 | 58 |
| 7.5 kg/ha Ato Cide | 3 | 5 | 77 | 58 |
| 10 kg/ha Ato Cide | 6 | 12 | 54 | 0 |
| 0.6 kg/ha Azoxystrobin | 9 | 10 | 31 | 17 |

LEGEND: kg = kilograms; ha = hectares.

Raw data were transformed using conservative statistical methods that do pairwise comparisons.

Results:

No phytotoxicity was observed at any dosage of Ato Cide. Ato Cide at both 500 ppm PAA (5 kg/ha) and 750 ppm PAA (7.5 kg/ha) reduced disease incidence by 60-85% relative to the water-sprayed inoculated control. Azoxystrobin reduced disease incidence by only 15-30% relative to the water-sprayed inoculated control. Ato Cide at both 500 ppm PAA (5 kg/ha) and 750 ppm PAA (7.5 kg/ha) maintained grass vigour at 7-8 (where 9 is the best). Azoxystrobin maintained grass vigour at a rating of only 4-5.

Example 10

Formulation of a Powdered Composition That Releases Peracetic Acid at Faster Rates when Dissolved in Water The following example illustrates a further alternative embodiment of the invention to the use of a surfactant and higher alkalinity for enhancing the release of peracetic acid in an aqueous solution of a powdered composition. This formula accommodates growers needs under certain conditions (i.e. weather, rain) and helps them to apply the product whenever they want with no delay in time caused by the maturation and slower generation of peracetic acid.

TABLE 15

Formulation of a powdered composition (Formula v2) that generates peracetic acid at faster and enhanced rates when dissolved in water.

| | |
|---|---|
| • Sodium percarbonate coated | 50% w/w |
| • TAED | 20% w/w |
| • KASIL SS (potassium silicate) | 10% w/w |
| • Citric acid | 15% w/w |
| • Bioterge AS 90 | 4% w/w |
| • EDTA | 1% w/w |

50 grams of sodium percarbonate coated were mixed with 20 grams TAED (Warwick) for 5 minutes; then 10 grams of Kasil SS (potassium silicate) were added and mixed for 5 minutes; then 15 grams of citric acid were added and mixed for 5 minutes; then, 4 grams of Bioterge AS 90 (surfactant) were added and mixed for 5 minutes; finally, 1 gram of EDTA was added and mixed for 10 minutes.

2 grams of this formula were dissolved in 1 L water.

The results obtained were the following:

| | Formula V2: Generation of peracetic acid at faster and enhanced rates (2 gr per liter) |
|---|---|
| August 5:11:00 (time zero) | |
| August 5:11:01 | PAA strip (LaMotte), PAA active; pH: 9.45 |
| August 5:11:03 | 12 drops 180 ppm |
| August 5:11:08 | 15 drops 225 ppm |
| August 5:11:22 | 18 drops 270 ppm |
| August 5:12:05 | 22 drops 330 ppm |
| August 5:12:49 | 18 drops 270 ppm |
| August 5:13:24 | 20 drops 300 ppm |
| August 5:14:25 | 16 drops 240 ppm |
| August 5:16:08 | 15 drops 225 ppm |
| August 5:16:30 | 15 drops 225 ppm; H2O2: 400 ppm |
| August 5:19:00 | 13 drops 195 ppm (after 7 hours) |
| August 5:19:10 | 13 drops 195 ppm (after 8 hours) |
| August 5:21:40 | 11 drops 165 ppm |
| August 5:23:00 | 13 drops 150 ppm (after 12 hours) |
| August 6:09:00 | 7 drops 105 ppm |
| August 6:11:00 | 6 drops 90 ppm (after 24 hours) |
| August 7:11:00 | 1 drops 15 ppm (after 48 hours) |

The above formula V2 generates the peracetic acid faster, that is in less than one hour when compare with the ATO CIDE formulation of Example 1 described hereinabove. This is the result of the addition of a surfactant which enhances the release of peracetic acid. The pH of 0.2 solution of formula V2 is: 9.00±1.5. The goal of this formula was to meet with the requirements of some growers who may decide to apply the fungicide as soon as they observe a disease on their plants, and cannot wait few hours for peracetic acid generation.

Example 11

Formulation of a Powdered Composition that Releases Peracetic Acid at Alkaline Levels and Faster Rates when Dissolved in Water This example illustrates another alternative embodiment of the invention to meet the objective described in example 10. More particularly, the present example illustrates that an alkaline formula allows to generate peracetic acid at faster rate.

TABLE 16

Formulation of a powdered composition (Alkaline formula) that generates peracetic acid at alkaline levels and faster rates when dissolved in water without the pH adjusting ingredient.

| | |
|---|---|
| • Sodium percarbonate coated | 69.5% w/w |
| • TAED | 20% w/w |
| • KASIL SS (potassium silicate) | 10% w/w |
| • EDTA | 0.5% w/w. |

69.5 grams of sodium percarbonate coated were mixed with 20 grams TAED (Warwick) for 5 minutes; then 10 grams of Kasil SS (potassium silicate) were added and mixed for 5 minutes; finally, 0.5 gram of EDTA was added and mixed for 10 minutes.

2 grams of this formula were dissolved in 1 L water.

Results obtained were the following:

| August 2:2:45 (time zero) | Alkaline formula (2 gr per liter) | |
|---|---|---|
| August 2:2:47 | 11 drops | 300 ppm PAA |
| August 2:2:53 | 12 drops | 270 ppm PAA; Ph = 10.4 |
| August 2:2:59 | 14 drops | |
| August 2:3:00 | pH = 10.6 | |
| August 2:3:02 | 14 drops | 700 ppm H2O2 |
| August 2:3:05 | 12 drops | 180 ppm PAA |
| August 2:3:11 | 9 drops | 135 ppm PAA |
| August 2:3:15 | 10 drops | 150 ppm PAA |
| August 2:3:22 | 6 drops | 90 ppm PAA |
| August 2:3:33 | 2 drops | 30 ppm PAA |

The alkaline formula generates peracetic acid at faster rates; however peracetic acid decomposes also very fast.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for controlling pathogens on a plant tissue of a growing plant having roots and leaves, said method comprising treating said growing plant with an aqueous solution resulting from the dissolution in water of a composition comprising a water soluble mixture of (i) a peracetic acid precursor comprising: a) hydrogen peroxide, hydrogen peroxide precursor or a mixture thereof, b) optionally a pH adjusting agent, and c) an acetylating agent; and (ii) at least one SAR inducer which is a water soluble silicate salt defining a source of silicate ions; wherein said composition generates peracetic acid (PAA) upon addition of water, the resulting aqueous solution comprising peracetic acid at a concentration and a pH which are not harmful for said plant tissue and at least one SAR inducer which is a water soluble silicate salt defining a source of silicate ions, and and wherein said treatment is optionally repeated according to a predetermined schedule, synergistic effect being observed once the SAR inducer which is a water soluble silicate salt defining a source of silicate ions, and the peracetic acid are respectively simultaneously present in and on the plant.

2. The method of claim 1, wherein pathogens are selected from the group consisting of viruses, bacteria, fungus, yeasts and molds.

3. The method of claim 2, wherein bacteria are *Xanthomonas*.

4. The method of claim 1, wherein said aqueous solution is sprayed onto the leaves of the growing plant, and a substrate comprising roots of said growing plant, and wherein the at least one SAR inducer which is a water soluble silicate salt defining a source of silicate ions, is absorbed by leaves and the roots of the growing plant.

5. The method of claim 4, wherein the water soluble silicate salt defining a source of silicate ions is potassium silicate, sodium silicate, sodium metasilicate, or a mixture thereof.

6. The method of claim 5, wherein the water soluble silicate salt defining a source of silicate ions is potassium silicate.

7. The method of claim 1, wherein the growing plant is selected from the group consisting of those producing fruits, nuts, cereals, vegetables or flowers.

8. A method for controlling pathogens on a plant tissue of a growing plant having roots and leaves, said method comprising treating said growing plant with an aqueous solution resulting from the dissolution in water of the powdered composition comprising a dry, water soluble mixture of
(i) a peracetic acid precursor comprising:
a) a solid hydrogen peroxide precursor,
b) optionally a pH adjusting agent, and
c) an acetylating agent; and
(ii) at least one SAR inducer which is a water soluble silicate salt defining a source of silicate ions;
wherein said composition generates in situ peracetic acid (PAA) upon addition of water, the resulting aqueous solution comprising the peracetic acid at a concentration and a pH which are not harmful for said plant tissue and the at least one SAR inducer, and wherein said treatment is optionally repeated according to a predetermined schedule, a synergistic effect being observed once the SAR inducer, and the peracetic acid are respectively simultaneously present in and on the plant.

9. The method of claim 8, wherein the pathogens are selected from the group consisting of viruses, bacteria, fungus, yeasts and molds, wherein said aqueous solution is sprayed onto the leaves of the growing plant, and a substrate comprising roots of said growing plant, wherein the at least one SAR inducer is absorbed by leaves and the roots of the growing plant, and wherein the at least one SAR inducer is potassium silicate, sodium silicate, sodium metasilicate, or a mixture thereof.

10. The method of claim 9, wherein the water soluble silicate salt is potassium silicate.

11. The method of claim 9, wherein the bacteria are *Xanthomonas*.

12. The method of claim 9, wherein the growing plant is selected from the group consisting of those producing fruits, nuts, cereals, vegetables and flowers.

13. The method of claim 9, wherein the growing plant is a plant producing a fruit selected from the group consisting of apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive and lime.

14. The method of claim 9, wherein the growing plant is a plant producing a vegetable selected from the group consisting of artichoke, bean, beetroot, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip and peanut.

15. The method of claim 9, wherein the growing plant is a plant producing a cereal.

16. The method of claim 15, wherein the cereal is amaranth, breadnut, barley, buckwheat, canola, corn, fonio, kamut, millet, oats, *quinoa*, cattail, chia, flax, kañiwa pitseed goosefoot, wattleseed, rice, rye, sorghum, spelt, teff, triticale, wheat, or colza.

17. The method of claim 9, wherein the growing plant is a plant producing a nut selected from the group consisting of almond, beech nut, Brazil nut, butternut, cashew, chestnut, chinquapin, filbert, hickory nut, macadamia nut, pecan, walnut and pistachio.

18. The method of claim 9, wherein the growing plant is turf grass or long grass.

19. The method of claim 9, wherein the growing plant is a plant producing a tomato.

20. The method of claim 9, wherein the growing plant has at least a plant tissue that is selected from the group consisting of a leaf, a stem, a flower, a fruit, a tuber, a rhizome, a corm, a root and combinations thereof.

21. The method of claim 8, wherein the dry, water soluble mixture comprises:
(i)-a) about 30-60% w/w of the solid hydrogen peroxide precursor,
(i)-b) about 10-40% w/w the pH adjusting agent,
(i)-c) about 10-40% w/w of the acetylating agent;
(ii) about 1-30% w/w of the at least one SAR inducer which is the water soluble silicate salt defining a source of silicate ions;
(iii) optionally from 0.01 to 10% w/w of a sequestering agent; and
(iv) optionally at least one surfactant;
wherein (i)-a), (i)-b) and (i)-c) represent the peracetic acid precursor; and wherein when 2 g of said dry, water soluble mixture of (i)-a), (i)-b), (i)-c), (ii), optionally (iii), and optionally (iv) is admixed with 1000 g of water, about 100 to 250 ppm of peracetic acid (PAA) are generated in situ at pH 7.0±2.

22. The method of claim 21, wherein:
the optional at least one surfactant is:
an anionic surfactant selected from the group consisting of carboxylates, sulfonates, petroleum sulfonates, alkylbenzenesulfonates, naphthalene sulphonates, olefin sulphonates, alkyl sulphates, sulphated natural oils, sulphated natural fats, sulphated esters, sulphated alkanolamides, sulphated alkanolamides, alkylphenols ethoxylated and alkylphenols sulphated; or
a non-ionic surfactant selected from the group consisting of ethoxylated aliphatic alcohol, polyoxyethylene surfactants, carboxylic esters, polyethylene glycol esters, anhydrosorbitol ester and its ethoxylated derivarives, glycol esters of fatty acids, carboxylic amides, monoalkanolamine condensates and polyoxyethylene fatty acid amides; or
a cationic surfactant selected from the group consisting of quarternary ammonium salts, amines with amide linkages, polyoxyethylene alkyl and alicyclic amines, 4-N,N,N',N'-tetrakis substituted ethylenediamines and 5,2-alkyl-1-hydroxyethyl 2-imidazolines; or
an amphoteric surfactant selected from the group consisting of N-coco 3-aminopropionic acid and its sodium salt, N-tallow 3-iminodipropionate and its disodium salt, N-carboxymethyl N-dimethyl N-9 octadecenyl ammonium hydroxide, and N-cocoamidethyl N-hydroxyethylglycine and its sodium salt;
the optional sequestering agent is EDTA, NTA, DTPA, or Phosphonates; or
the optional sequestering agent is ethylenediaminetetraacetic acid (EDTA), nitrilotriacetic Acid (NTA), diethylene triamine pentaacetic acid (DTPA), 1-hydroxyethane(1,1-diylbiphosphonic acid) (HEDP), nitrilotris(methylenephosphonic acid) (NTMP), diethylenetriaminepentakis(methylenephosphonic acid) (DTPMP), 1,2-diaminoethanetetrakis(methylenephosphonic acid) (EDTMP), sodium salt of 1,2-diaminoethanetetrakis(methylenephosphonic acid), potassium salt of 1,2-diaminoethanetetrakis(methylenephosphonic acid), ammonium salt of 1,2-diaminoethanetetrakis(methylenephosphonic acid), amino trimethylene phosphonic acid (ATMP), ethylene diamine tetra (methylene phosphonic acid) (EDTMPA Solid), phosphonobutane tricarboxylic acid, (PBTCA), polyhydric alcohol phosphate ester (PAPE), 2-hydroxyphosphonocarboxylic acid (HPAA), hexamethylenediaminetetra(methylenephosphonic acid) HMDTMPA, or mixtures thereof; or
the optional sequestering agent is selected from the group consisting of ethylenediaminetetraacetic acid (EDTA), nitrilotriacetic acid (NTA), phosphonates, citric acid, phosphoric acid, sulfuric acid, dipicolinic acid, sulfonic acid, and boric acid, or mixture thereof;
the solid hydrogen peroxide precursor is a persalt, said persalt being sodium perborate, sodium percarbonate, ammonium percarbonate, sodium peroxyhydrate, calcium peroxide, sodium peroxide, sodium perborate monohydrate, sodium perborate tetrahydrate, sodium persulfate, potassium monopersulfate, perphosphate, magnesium peroxide, zinc peroxide, urea hydrogen peroxide, perhydrate of urea, thiourea dioxide, or mixtures thereof;
the pH adjusting agent is sulfuric acid, citric acid, phosphoric acid, nitric acid, hydrochloric acid, glycolic acid, formic acid, acetic acid, hydrofluoric acid, nitrous acid, hydrocyanic acid, benzoic acid, carboxylic acid, lactic acid, acetic acid, oxalic acid, sulfamic acid, phosphorous acid, dipicolinic acid, urea.HCl, boric acid, or mixtures thereof; and
the at least one SAR inducer is potassium silicate, sodium silicate, sodium metasilicate, or a mixture thereof.

23. The method of claim 8, the powdered composition comprises a dry, water soluble mixture of:
(i)-a) about 43.5% w/w of a sodium percarbonate as said solid hydrogen peroxide,
(i)-b) about 25% w/w a citric acid as said pH adjusting agent,
(i)-c) about 21% w/w of tetraacetylethylenediamine (TAED) as said acetylating agent;
(ii) about 10% w/w of potassium silicate as said at least one SAR inducer which is the water soluble silicate salt defining a source of silicate ions; and
(iii) about 0.5% w/w of ethylenediaminetetraacetic acid (EDTA) as a sequestering agent.

24. The method of claim 8, wherein the powdered composition comprises a dry, water soluble mixture of:
(i)-a) about 50% w/w of a sodium percarbonate as said solid hydrogen peroxide,
(i)-b) about 15% w/w a citric acid as said pH adjusting agent,
(i)-c) about 20% w/w of tetraacetylethylenediamine (TAED) as said acetylating agent;
(ii) about 10% w/w of potassium silicate as said at least one SAR inducer which is the water soluble silicate salt defining a source of silicate ions;
(iii) about 1% w/w of ethylenediaminetetraacetic acid (EDTA) as a sequestering agent; and
(iv) about 4% w/w of an alpha olefin sulfonate having 12 to 18 carbon atoms.

* * * * *